United States Patent [19]

Kirsten et al.

[11] Patent Number: 4,802,910
[45] Date of Patent: Feb. 7, 1989

[54] HERBICIDAL ACYLATED SULPHONYLGUANIDINES

[75] Inventors: Rolf Kirsten, Monheim; Joachim Kluth, Langenfeld; Klaus-Helmut Müller, Düsseldorf; Theodor Pfister, Monheim; Hans-Jochem Riebel, Wuppertal; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 5,539

[22] Filed: Jan. 20, 1987

[30] Foreign Application Priority Data

Jan. 30, 1986 [DE] Fed. Rep. of Germany ....... 3602679

[51] Int. Cl.$^4$ .................. A01N 43/66; C07D 251/46; C07D 251/52; C07D 251/18
[52] U.S. Cl. .......................................... 71/93; 71/90; 544/113; 544/211; 544/212; 544/197; 544/198; 544/206; 544/207; 544/208; 544/209; 544/194; 544/204; 544/205; 544/196; 544/199; 544/210; 544/213
[58] Field of Search .................. 71/93, 90; 544/113, 544/211, 212, 197, 198, 206, 207, 208, 209, 194, 204, 205, 196, 199, 210, 213

[56] References Cited

U.S. PATENT DOCUMENTS

| | | | |
|---|---|---|---|
| 4,559,079 | 12/1985 | Shiokawa et al. | 71/92 |
| 4,568,381 | 2/1986 | Saito et al. | 544/211 |
| 4,602,938 | 7/1986 | Moriya et al. | 71/93 |
| 4,689,070 | 8/1987 | Shapiro | 71/90 |

FOREIGN PATENT DOCUMENTS 0117014 8/1984 European Pat. Off. .

Primary Examiner—John M. Ford
Attorney, Agent, or Firm—Sprung Horn Kramer & Woods

[57] ABSTRACT

Novel herbicides of the formula

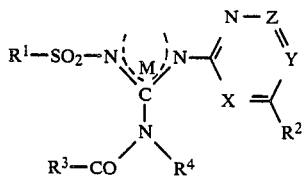

in which
$R^1$ represents an organic radical,
$R^2$ represents hydrogen or an organic radical,
$R^3$ represents an organic radical or an amino radical,
$R^4$ represents hydrogen, an organic radical, an ether radical or an amino radical,
X represents N or CH,
Y and Z each represent N, CH or a substituted C radical, and
M is H, a metal ion or an acyl radical, or a strong acid adduct thereof. Some intermediates are also new.

10 Claims, No Drawings

HERBICIDAL ACYLATED SULPHONYLGUANIDINES

The invention relates to new acylated sulphonylguanidines, processes and new intermediate products for their preparation and their use as herbicides.

It is known that certain guanidines, such as, for example, N'-(4,6-dimethyl-pyrimidin-2-yl)-N'''-hydroxy-N'''-(2-chloro-benzenesulphonyl)-guanidine, have a herbicidal action. However, the action of these compounds is not always completely satisfactory (compare EP-OS (European Published Specification) No. 117,014).

New acylated sulphonylguanidines of the general formula (I)

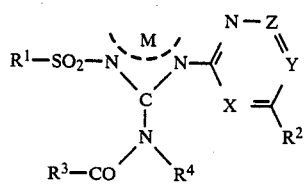

in which
- $R^1$ represents an optionally substituted radical from the series comprising alkyl, aralkyl and aryl with in each case up to 10 carbon atoms, or represents an optionally substituted and/or optionally fused five- or six-membered heterocyclic radical which contains an oxygen or a sulphur atom and/or 1 or 2 nitrogen atoms,
- $R^2$ represents hydrogen, halogen, hydroxyl, $C_1$-$C_4$-alkyl, $C_1$-$C_4$-halogenoalkyl, $C_1$-$C_4$-alkoxy, $C_1$-$C_4$-halogenoalkoxy, $C_1$-$C_4$-alkylthio, $C_1$-$C_4$-halogenoalkylthio, amino, $C_1$-$C_4$-alkylamino or di-($C_1$-$C_4$-alkyl)-amino,
- X represents nitrogen or a —CH— grouping,
- Y represents nitrogen or a —CR$^5$— grouping,
wherein
- $R^5$ represents hydrogen, halogen, cyano, $C_1$-$C_4$-alkyl, formyl, $C_1$-$C_4$-alkyl-carbonyl or $C_1$-$C_4$-alkoxy-carbonyl,
- Z represents nitrogen or a —CR$^6$— grouping, wherein
- $R^6$ represents hydrogen, halogen, hydroxyl, $C_1$-$C_4$-alkyl, $C_1$-$C_4$-alkoxy, $C_1$-$C_4$-alkylthio, $C_1$-$C_4$-alkylamino or di-($C_1$-$C_4$-alkyl)-amino,
and in which, furthermore,
- $R^3$ represents a radical $R^7$, or represents a radical —NHR$^8$,
wherein
- $R^7$ represents an optionally substituted radical from the series comprising alkyl, alkenyl, alkinyl, alkoxy, alkenyloxy, alkinyloxy, cycloalkyl, dialkylamino, aralkyl, aryl, aralkoxy, aryloxy, alkylthio, aralkylthio and arylthio with in each case up to 10 carbon atoms and
- $R^8$ represents an optionally substituted radical from the series comprising alkyl, cycloalkyl, aralkyl, aryl and arylsulphonyl with in each case up to 10 carbon atoms,
and in which, furthermore,
- $R^4$ represents hydrogen, or represents an optionally substituted radical from the series comprising alkyl, alkenyl, alkinyl, cycloalkyl, aralkyl and aryl with in each case up to 10 carbon atoms, or
- $R^4$ represents the radical —OR$^9$,
wherein
- $R^9$ represents hydrogen or an optionally substituted radical from the series comprising alkyl, alkenyl, alkinyl, cycloalkyl, cycloalkylalkyl, aralkyl and aryl with in each case up to 10 carbon atoms,
or in which, furthermore,
- $R^4$ represents the radical —NR$^{10}$R$^{11}$,
wherein
- $R^{10}$ represents hydrogen or optionally substituted $C_1$-$C_4$-alkyl and
- $R^{11}$ represents hydrogen or an optionally substituted radical from the series comprising alkyl, alkenyl, alkinyl, cycloalkyl, aralkyl, aryl, alkylcarbonyl, alkoxycarbonyl, alkylsulphonyl and arylsulphonyl with in each case up to 10 carbon atoms, or represents an optionally substituted five- or six-membered aromatic heterocyclic radical which contains an oxygen or sulphur atom and/or 1 to 3 nitrogen atoms, and
- M represents hydrogen or one equivalent of a metal or represents the radical —COR$^7$,
wherein
- $R^7$ has the abovementioned meanings, and adducts of the compounds of the formula (I) with strong acids, have now been found.

If M represents hydrogen, the general formula (I) represents the individual tautomers of the formulas (IA) and (IB)

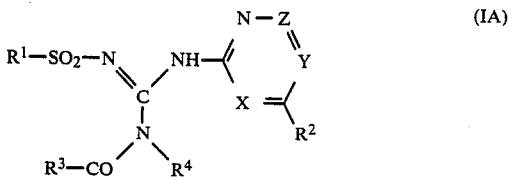

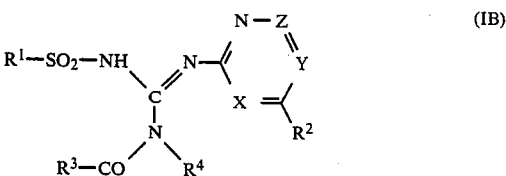

in which
X, Y, Z, $R^1$, $R^2$, $R^3$ and $R^4$ have the abovementioned meanings,
and mixtures of the tautomers (IA) and (IB).

The mixing ratio depends on factors which determine the state of aggregation, such as, for example, the temperature, solvent and concentration.

In the case where M represents the radical —COR$^7$, the following isomers of the formulas (IC) and (ID) are possible:

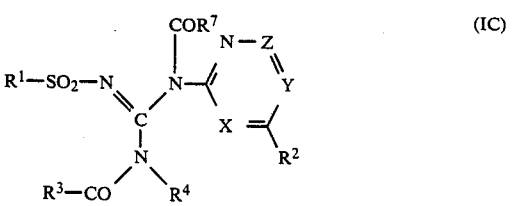

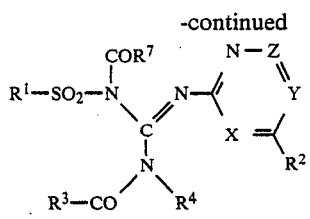
(ID)

in which
X, Y, Z, $R^1$, $R^2$, $R^3$, $R^4$ and $R^7$ have the above-mentioned meanings.

The new acylated sulphonylguanidines of the formula (I) are obtained (a) in the case where $R^3$ represents the radical $R^7$, wherein $R^7$ has the abovementioned meanings, and M represents hydrogen, by a process in which sulphonylguanidine derivatives of the formula (II)

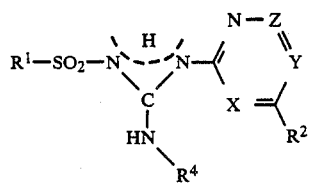
(II)

in which
X, Y, Z, $R^1$, $R^2$ and $R^4$ have the abovementioned meanings,
are reacted with acylating agents of the formula (III)

$$R^7COW \quad (III)$$

in which
W represents halogen, or represents the radical $R^7COO-$ and
$R^7$ has the abovementioned meanings,
if appropriate in the presence of acid acceptors and if appropriate in the presence of diluents; or (b) in the case where $R^3$ represents the radical $-NHR^8$, wherein $R^8$ has the abovementioned meanings and M represents hydrogen, by a process in which sulphonylguanidine derivatives of the formula (II)

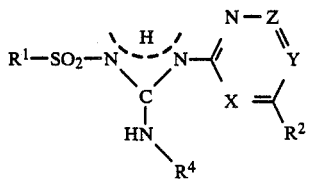
(II)

in which
X, Y, Z, $R^1$, $R^2$ and $R^4$ have the abovementioned meanings,
are reacted with isocyanates of the formula (IV)

$$R^8-NCO \quad (IV)$$

in which
$R^8$ has the abovementioned meanings,
if appropriate in the presence of catalysts and if appropriate in the presence of diluents; or (c) in the case where M represents hydrogen, by a process in which guanidine derivatives of the formula (V)

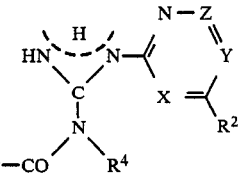
(V)

in which
X, Y, Z, $R^2$, $R^3$ and $R^4$ have the abovementioned meanings,
are reacted with sulphonyl chlorides of the formula (VI)

$$R^1-SO_2Cl \quad (VI)$$

in which
$R^1$ has the abovementioned meanings,
in the presence of acid acceptors and if appropriate in the presence of diluents; or (d) in the case where M represents one equivalent of a metal, by a process in which the compounds of the formula (I) obtainable by the processes described above under (a), (b) and (c), in which M represents hydrogen and X, Y, Z, $R^1$, $R^2$, $R^3$ and $R^4$ have the abovementioned meanings, are reacted with metal hydroxides, hydrides or alkanolates or with organometallic compounds, if appropriate in the presence of diluents; or (e) in the case where 1:1 adducts of compounds of the formula (I) with strong acids are to be prepared, by a process in which compounds of the formula (I) in which M represents hydrogen and X, Y, Z, $R^1$, $R^2$, $R^3$ and $R^4$ have the abovementioned meanings are reacted with strong acids, if appropriate in the presence of diluents; or (f) in the case where M represents the radical $R^7CO-$, wherein $R^7$ has the abovementioned meanings, (α) by a process in which the compounds of the formula (I) obtainable by the processes described above under (a), (b) and (c) in which M represents hydrogen and X, Y, Z, $R^1$, $R^2$, $R^3$ and $R^4$ have the abovementioned meanings, are reacted with acylating agents of the formula (III)

$$R^7COW \quad (III)$$

in which
W and $R^7$ have the abovementioned meanings,
if appropriate in the presence of acid acceptors and if appropriate in the presence of diluents, or (β) by a process in which sulphonylguanidine derivatives of the formula (II)

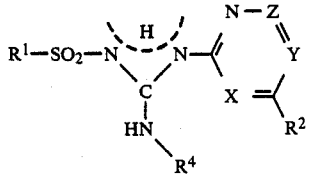
(II)

in which
X, Y, Z, $R^1$, $R^2$ and $R^4$ have the abovementioned meanings, are reacted with at least twice the molar amount of acylating agents of the formula (III)

$$R^7COW \quad (III)$$

in which

W and $R^7$ have the abovementioned meanings, in the presence of acid acceptors and if appropriate in the presence of diluents.

The new acylated sulphonylguanidines of the formula (I) and their adducts with strong acids are distinguished by a potent herbicidal activity.

Surprisingly, the new compounds of the formula (I) exhibit a considerably better herbicidal action than the already known guanidines of the same type of action.

The invention preferably relates to compounds of the formula (I) in which $R^1$ represents the radical

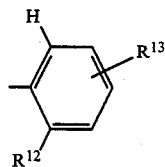

wherein $R^{12}$ and $R^{13}$ are identical or different and represent hydrogen, halogen [such as, in particular, fluorine, chlorine, bromine and/or iodine], cyano, nitro or $C_1$-$C_6$-alkyl [which is optionally substituted by fluorine, chlorine, bromine, cyano, carboxyl, $C_1$-$C_4$-alkoxycarbonyl, $C_1$-$C_4$-alkyl-amino-carbonyl, di-($C_1$-$C_4$-alkyl)-amino-carbonyl, hydroxyl, $C_1$-$C_4$-alkoxy, formyloxy, $C_1$-$C_4$-alkyl-carbonyloxy, $C_1$-$C_4$-alkoxy-carbonyloxy, $C_1$-$C_4$-alkylamino-carbonyloxy, $C_1$-$C_4$-alkylthio, $C_1$-$C_4$-alkylsulphinyl, $C_1$-$C_4$-alkylsulphonyl, di-($C_1$-$C_4$-alkyl)-aminosulphonyl, $C_3$-$C_6$-cycloalkyl or phenyl], or represent $C_2$-$C_6$-alkenyl [which is optionally substituted by fluorine, chlorine, bromine, cyano, $C_1$-$C_4$-alkoxy-carbonyl, carboxyl or phenyl], or represent $C_2$-$C_6$-alkinyl [which is optionally substituted by fluorine, chlorine, bromine, cyano, $C_1$-$C_4$-alkoxy-carbonyl, carboxyl or phenyl], or represent $C_1$-$C_4$-alkoxy [which is optionally substituted by fluorine, chlorine, bromine, cyano, carboxyl, $C_1$-$C_4$-alkoxy-carbonyl, $C_1$-$C_4$-alkoxy, $C_1$-$C_4$-alkylthio, $C_1$-$C_4$-alkylsulphinyl or $C_1$-$C_4$-alkylsulphonyl], or represent $C_1$-$C_4$-alkylthio [which is optionally substituted by fluorine, chlorine, bromine, cyano, carboxyl, $C_1$-$C_4$-alkoxycarbonyl, $C_1$-$C_4$-alkylthio, $C_1$-$C_4$-alkylsulphinyl or $C_1$-$C_4$-alkylsulphonyl], or represent $C_3$-$C_6$-alkenyloxy [which is optionally substituted by fluorine, chlorine, bromine, cyano or $C_1$-$C_4$-alkoxy-carbonyl], or represent $C_2$-$C_6$-alkenylthio [which is optionally substituted by fluorine, chlorine, bromine, cyano, nitro, $C_1$-$C_3$-alkylthio or $C_1$-$C_4$-alkoxycarbonyl], $C_3$-$C_6$-alkinyloxy or $C_3$-$C_6$-alkinylthio, or represent the radical —S(O)$_p$—$R^{14}$, wherein p represents the number 1 or 2 and $R^{14}$ represents $C_1$-$C_4$-alkyl [which is optionally substituted by fluorine, chlorine, bromine, cyano or $C_1$-$C_4$-alkoxy-carbonyl], $C_3$-$C_6$-alkenyl, $C_3$-$C_6$-alkinyl, $C_1$-$C_4$-alkoxy, $C_1$-$C_4$-alkoxy-amino, $C_1$-$C_4$-alkoxy-$C_1$-$C_4$-alkylamino, $C_1$-$C_4$-alkylamino or di-($C_1$-$C_4$-alkyl)-amino, or $R^{12}$ and $R^{13}$ furthermore represent phenyl or phenoxy, or represent $C_1$-$C_4$-alkylcarbonylamino, $C_1$-$C_4$-alkoxy-carbonylamino, $C_1$-$C_4$-alkylaminocarbonyl-amino or di-($C_1$-$C_4$-alkyl)-amino-carbonylamino, or represent the radical —CO—$R^{15}$, wherein $R^{15}$ represents $C_1$-$C_6$-alkyl, $C_1$-$C_6$-alkoxy, $C_3$-$C_6$-cycloalkoxy, $C_3$-$C_6$-alkenyloxy, $C_1$-$C_4$-alkylthio, $C_1$-$C_4$-alkylamino, $C_1$-$C_4$-alkoxyamino, $C_1$-$C_4$-alkoxy-$C_1$-$C_4$-alkyl-amino or di-($C_1$-$C_4$-alkyl)-amino [which are optionally substituted by fluorine and/or chlorine], or $R^{12}$ and $R^{13}$ furthermore represent $C_1$-$C_4$-alkyl-sulphonyloxy or di-($C_1$-$C_4$-alkyl)-aminosulphonyl-amino, or represent the radical —CH=N—$R^{16}$, wherein $R^{16}$ represents $C_1$-$C_6$-alkyl which is optionally substituted by fluorine, chlorine, cyano, carboxyl, $C_1$-$C_4$-alkoxy, carbonyl, $C_1$-$C_4$-alkylthio, $C_1$-$C_4$-alkylsulphinyl or $C_1$-$C_4$-alkylsulphonyl, or represents benzyl which is optionally substituted by fluorine or chlorine, or represents $C_3$-$C_6$-alkenyl or $C_3$-$C_6$-alkinyl, each of which is optionally substituted by fluorine or chlorine, or represents phenyl which is optionally substituted by fluorine, chlorine, bromine, $C_1$-$C_4$-alkyl, $C_1$-$C_4$-alkoxy, trifluoromethyl, trifluoromethoxy or trifluoromethylthio, or represents $C_1$-$C_6$-alkoxy, $C_3$-$C_6$-alkenoxy, $C_3$-$C_6$-alkinoxy or benzyloxy, each of which is optionally substituted by fluorine and/or chlorine, or represents amino, $C_1$-$C_4$-alkylamino, di-($C_1$-$C_4$-alkyl)-amino, phenylamino, $C_1$-$C_4$-alkyl-carbonyl-amino, $C_1$-$C_4$-alkoxy-carbonylamino or $C_1$-$C_4$-alkylsulphonylamino, or represents phenylsulphonylamino which is optionally substituted by fluorine, chlorine, bromine or methyl, or wherein, furthermore, $R^1$ represents the radical

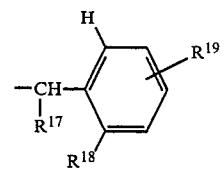

wherein $R^{17}$ represents hydrogen or $C_1$-$C_4$-alkyl and $R^{18}$ and $R^{19}$ are identical or different and represent hydrogen, fluorine, chlorine, bromine, nitro, cyano, $C_1$-$C_4$-alkyl [which is optionally substituted by fluorine and/or chlorine], $C_1$-$C_4$-alkoxy [which is optionally substituted by fluorine and/or chlorine], carboxyl, $C_1$-$C_4$-alkoxy-carbonyl, $C_1$-$C_4$-alkylsulphonyl or di-($C_1$-$C_4$-alkyl)-aminosulphonyl;

or wherein, furthermore, $R^1$ represents the radical

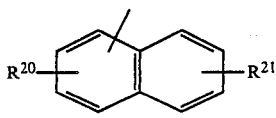

wherein
R²⁰ and R²¹ are identical or different and represent hydrogen, fluorine, chlorine, bromine, nitro, cyano, C₁-C₄-alkyl [which is optionally substituted by fluorine and/or chlorine] or C₁-C₄-alkoxy [which is optionally substituted by fluorine and/or chlorine];

or wherein, furthermore,
R¹ represents the radical

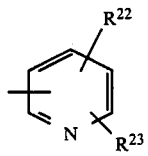

wherein
R²² and R²³ are identical or different and represent hydrogen, fluorine, chlorine, bromine, nitro, cyano, C₁-C₄-alkyl [which is optionally substituted by fluorine and/or chlorine] or C₁-C₄-alkoxy [which is optionally substituted by fluorine and/or chlorine], or represent C₁-C₄-alkylthio, C₁-C₄-alkylsulphinyl or C₁-C₄-alkylsulphonyl [which are optionally substituted by fluorine and/or chlorine], or represent di-(C₁-C₄-alkyl)-aminosulphonyl or C₁-C₄-alkoxycarbonyl;

or wherein, furthermore,
R¹ represents the radical

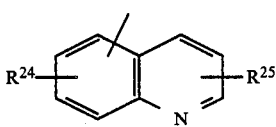

wherein
R²⁴ and R²⁵ are identical or different and represent hydrogen, fluorine, chlorine, bromine, C₁-C₄-alkyl [which is optionally substituted by fluorine and/or bromine] or C₁-C₄-alkoxy [which is optionally substituted by fluorine and/or chlorine], or represent C₁-C₄-alkylthio, C₁-C₄-alkylsulphinyl or C₁-C₄-alkylsulphonyl [which are optionally substituted by fluorine and/or chlorine], or represent di-(C₁-C₄-alkyl)-aminosulphonyl;

or wherein, furthermore,
R¹ represents the radical

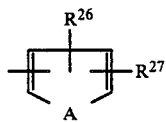

wherein
R²⁶ and R²⁷ are identical or different and represent hydrogen, fluorine, chlorine, bromine, cyano, nitro, C₁-C₄-alkyl [which is optionally substituted by fluorine and/or chlorine], C₁-C₄-alkoxy [which is optionally substituted by fluorine and/or chlorine], C₁-C₄-alkylthio, C₁-C₄-alkylsulphinyl or C₁-C₄-alkylsulphonyl [which are optionally substituted by fluorine and/or chlorine], di-(C₁-C₄-alkyl)-aminosulphonyl or C₁-C₄-alkoxy-carbonyl and A represents oxygen, sulphur or the grouping N—Z¹,
wherein
Z¹ represents hydrogen, C₁-C₄-alkyl [which is optionally substituted by fluorine, chlorine, bromine or cyano], C₃-C₆-cycloalkyl, benzyl, phenyl [which is optionally substituted by fluorine, chlorine, bromine or nitro], C₁-C₄-alkylcarbonyl, C₁-C₄-alkoxy-carbonyl or di-(C₁-C₄-alkyl)-aminocarbonyl;

or wherein, furthermore,
R¹ represents the radical

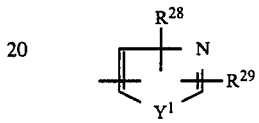

wherein
R²⁸ represents hydrogen, C₁-C₅-alkyl or halogen,
R²⁹ represents hydrogen or C₁-C₅-alkyl and
Y¹ represents sulphur or the grouping N—R³⁰,
R³⁰ represents hydrogen or C₁-C₅-alkyl,
and in which, furthermore,
R² represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino,
X represents nitrogen or a —CH— grouping,
Y represents nitrogen or a —CR⁵— grouping,
wherein
R⁵ represents hydrogen, fluorine, chlorine, bromine, cyano, methyl, formyl, acetyl, methoxycarbonyl or ethoxycarbonyl, and
Z represents nitrogen or a —CR⁶— grouping,
wherein
R⁶ represents hydrogen, fluorine, chlorine, bromine, methyl, ethyl, methoxy, ethoxy, propoxy, isopropoxy, methylthio, ethylthio, methylamino, ethylamino, dimethylamino or diethylamino,
and in which, furthermore,
R³ represents the radical R⁷, or represents a radical —NHR⁸,
wherein
R⁷ represents C₁-C₈-alkyl, C₁-C₈-alkoxy or C₁-C₈-alkylthio [which is optionally substituted by fluorine, chlorine, bromine, cyano, nitro, C₁-C₄-alkoxy-carbonyl, di-(C₁-C₄-alkyl)-aminocarbonyl, C₁-C₄-alkoxy, C₁-C₄-alkylthio, C₁-C₄-alkylsulphinyl or C₁-C₄-alkylsulphonyl], or represents C₂-C₈-alkenyl or C₂-C₈-alkinyl [which are optionally substituted by fluorine, chlorine, bromine, cyano, nitro, C₁-C₄-alkoxy, C₁-C₄-alkylthio or phenyl], or represents C₂-C₈-alkenyloxy or C₂-C₈-alkinyloxy [which are optionally substituted by fluorine, chlorine, bromine, cyano, nitro, C₁-C₄-alkoxy, C₁-C₄-alkylthio or phenyl], or represents C₃-C₆-cycloalkyl or di-(C₁-C₄-alkyl)-amino [which is optionally substituted by fluorine, chlorine, bromine, cyano, nitro, phenyl, phenoxy, C₁-C₄-alkoxy, C₁-C₄-alkyltho, C₁-C₄-alkylsulphinyl or $C_1$-$C_4$-alkylsulphonyl], or represents phenoxy or benzyloxy, or represents phenylthio or benzylthio [which are optionally substituted by fluorine, chlorine, bromine, $C_1$-$C_4$-alkyl, trifluoromethyl, $C_1$-$C_4$-alkoxy, $C_1$-$C_2$-fluoroalkoxy, $C_1$-$C_4$-alkylthio, $C_1$-$C_4$-alkylsulphinyl, $C_1$-$C_4$-alkylsulphonyl, cyano, nitro and/or $C_1$-$C_4$-alkoxycarbonyl], or represents benzyl or phenyl {which are optionally substituted by one or more radicals from the series comprising halogen, cyano, nitro, $C_1$-$C_4$-alkyl [which is optionally substituted by fluorine, chlorine, bromine, cyano, carboxyl, $C_1$-$C_4$-alkoxy-carbonyl, di-($C_1$-$C_4$-alkyl)-aminocarbonyl, $C_1$-$C_4$-alkoxy, formyloxy, $C_1$-$C_4$-alkylcarbonyloxy, $C_1$-$C_4$-alkoxy-carbonyloxy, $C_1$-$C_4$-alkylthio, $C_1$-$C_4$-alkylsulphinyl, $C_1$-$C_4$-alkylsulphonyl, di-($C_1$-$C_4$-alkyl)-amino-sulphonyl or phenyl], $C_2$-$C_6$-alkenyl [which is optionally substituted by fluorine, chlorine, bromine, cyano, $C_1$-$C_4$-alkoxycarbonyl, carboxyl or phenyl], $C_2$-$C_6$-alkinyl [which is optionally substituted by fluorine, chlorine, bromine, cyano, $C_1$-$C_4$-alkoxy-carbonyl or phenyl], $C_1$-$C_4$-alkoxy [which is optionally substituted by fluorine, chlorine, bromine, cyano, carboxyl, $C_1$-$C_4$-alkoxy-carbonyl, $C_1$-$C_4$-alkylthio, $C_1$-$C_4$-alkylsulphinyl or $C_1$-$C_4$-alkylsulphonyl], $C_3$-$C_6$-alkenoxy [which is optionally substituted by fluorine, chlorine, bromine, cyano or $C_1$-$C_4$-alkoxy-carbonyl], $C_3$-$C_6$-alkenylthio [which is optionally substituted by fluorine, chlorine, bromine, cyano or $C_1$-$C_4$-alkoxy-carbonyl], $C_1$-$C_4$-alkylthio, $C_1$-$C_4$-alkylsulphinyl or $C_1$-$C_4$-alkylsulphonyl [which are optionally substituted by fluorine, chlorine, bromine, cyano or $C_1$-$C_4$-alkoxycarbonyl], phenyl, phenoxy, di-($C_1$-$C_4$-alkyl)-amino-sulphonyl, $C_1$-$C_6$-alkoxy-carbonyl, $C_3$-$C_6$-cycloalkoxy-carbonyl or di-($C_1$-$C_4$-alkyl)-aminocarbonyl, and/or are optionally benzo-fused} and $R^8$ represents $C_1$-$C_6$-alkyl, cyclohexyl, benzyl, phenyl, naphthyl, phenylsulphonyl or naphthylsulphonyl (the aromatic radicals mentioned optionally being substituted by fluorine, chlorine, bromine, $C_1$-$C_4$-alkyl, $C_1$-$C_4$-alkoxy, trifluoromethyl, $C_1$-$C_2$-fluoroalkoxy, $C_1$-$C_2$-chlorofluoroalkoxy, $C_1$-$C_2$-chloroalkoxy, $C_1$-$C_4$-alkylthio, $C_1$-$C_4$-alkylsulphinyl, $C_1$-$C_4$-alkylsulphonyl, dimethylaminosulphonyl, N-methoxy-N-methyl-aminosulphonyl and/or $C_1$-$C_4$-alkoxycarbonyl);

and in which, furthermore, $R^4$ represents hydrogen, $C_1$-$C_6$-alkyl [which is optionally substituted by fluorine, chlorine, bromine, cyano, carboxyl, $C_1$-$C_4$-alkoxy-carbonyl, hydroxyl or $C_1$-$C_4$-alkoxy], $C_3$-$C_6$-cycloalkyl, $C_3$-$C_6$-alkenyl, $C_3$-$C_6$-alkinyl, phenylethyl or benzyl [which is optionally substituted by fluorine, chlorine, nitro, cyano, $C_1$-$C_4$-alkyl, $C_1$-$C_4$-alkoxy or $C_1$-$C_4$-alkoxy-carbonyl], or represents phenyl [which is optionally substituted by fluorine, chlorine, bromine, hydroxyl, cyano, nitro, amino, $C_1$-$C_4$-alkyl, trifluoromethyl, $C_1$-$C_4$-alkoxy, trifluoromethoxy, $C_1$-$C_4$-alkylthio, trifluoromethylthio, aminosulphonyl or $C_1$-$C_4$-alkoxy-carbonyl], or $R^4$ represents the radical —$OR^9$, wherein $R^9$ represents hydrogen, $C_1$-$C_8$-alkyl [which is optionally substituted by fluorine, chlorine, $C_1$-$C_4$-alkoxy, $C_1$-$C_4$-alkylthio, $C_1$-$C_4$-alkylsulphinyl, $C_1$-$C_4$-alkylsulphonyl, carboxyl, cyano or nitro], $C_3$-$C_6$-alkenyl [which is optionally substituted by fluorine or chlorine], $C_3$-$C_6$-alkinyl, $C_3$-$C_6$-cycloalkyl, $C_3$-$C_6$-cycloalkyl-$C_1$-$C_2$-alkyl, $C_1$-$C_4$-alkoxy-carbonyl-$C_1$-$C_2$-alkyl, aminocarbonyl-$C_1$-$C_2$-alkyl, $C_1$-$C_4$-alkylamino-carbonyl-$C_1$-$C_2$-alkyl, di-($C_1$-$C_4$-alkyl)amino-carbonyl-$C_1$-$C_2$-alkyl, or represents phenyl, phenylethyl, benzhydryl or benzyl [which are optionally substituted by fluorine, chlorine, bromine, cyano, nitro, $C_1$-$C_4$-alkyl, $C_1$-$C_4$-alkoxy, carboxyl or $C_1$-$C_4$-alkoxycarbonyl], or in which, furthermore, $R^4$ represents the radical

wherein $R^{10}$ represents hydrogen or $C_1$-$C_4$-alkyl and $R^{11}$ represents hydrogen, $C_1$-$C_4$-alkyl [which is optionally substituted by halogen, cyano, nitro, $C_1$-$C_4$-alkoxy or $C_1$-$C_4$-alkoxy-carbonyl], $C_3$-$C_6$-cycloalkyl, phenyl-$C_1$-$C_2$-alkyl or phenyl [which are optionally substituted by halogen, cyano, nitro, $C_1$-$C_4$-alkyl, $C_1$-$C_2$-halogenoalkyl, $C_1$-$C_4$-alkoxy, $C_1$-$C_2$-halogenoalkoxy, $C_1$-$C_4$-alkylthio, $C_1$-$C_2$-halogenoalkylthio or $C_1$-$C_4$-alkoxy-carbonyl], or represents $C_1$-$C_4$-alkyl-carbonyl, $C_1$-$C_4$-alkoxycarbonyl, $C_1$-$C_4$-alkylsulphonyl, $C_1$-$C_4$-halogenoalkylsulphonyl or phenylsulphonyl [which is optionally substituted by halogen, cyano, nitro, $C_1$-$C_4$-alkyl, $C_1$-$C_4$-halogenoalkyl, $C_1$-$C_4$-alkoxy, $C_1$-$C_2$-halogenoalkoxy or $C_1$-$C_4$-alkoxycarbonyl], or represents a pyrimidinyl radical and M represents hydrogen or one equivalent of sodium, potassium or calcium, or represents the radical —$COR^7$, wherein $R^7$ has the abovementioned preferred meanings.

The invention furthermore preferably relates to adducts of compounds of the formula (I)—as defined above—with hydrogen halide acids, such as hydrogen fluoride, hydrogen chloride, hydrogen bromide or hydrogen iodide, with sulphuric acid, with alkanesulphonic acids which have 1 to 4 carbon atoms and are optionally substituted by fluorine and/or chlorine, or with benzene- or naphthalenesulphonic acids which are optionally substituted by fluorine, chlorine, bromine or methyl.

The invention particularly relates to compounds of the formula (I)

in which (A) $R^1$ represents the radical

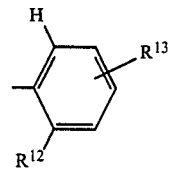

wherein $R^{12}$ represents fluorine, chlorine, bromine, methyl, trifluoromethyl, methoxy, difluoromethoxy, trifluoromethoxy, $C_1$–$C_3$-alkylthio, difluormethylthio, trifluoromethylthio, $C_1$–$C_3$-alkylsulphinyl, $C_1$–$C_3$-alkylsulphonyl, dimethylaminosulphonyl, diethylaminosulphonyl, N-methoxy-N-methylaminosulphonyl, phenyl, phenoxy, $C_1$–$C_3$-alkoxy-carbonyl, $C_1$—$C_3$-alkoxyamino-sulphonyl, $C_1$–$C_3$-alkoxyamino-carbonyl or $C_1$–$C_3$-alkylamino-carbonyl and $R^{13}$ represents hydrogen;
and wherein, furthermore, $R^2$ represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino, X represents nitrogen or a —CH— grouping,
Y represents nitrogen or a —CR$^5$— grouping,
wherein $R^5$ represents hydrogen, fluorine, chlorine, bromine, methyl, formyl, acetyl, methoxycarbonyl or ethoxycarbonyl, and Z represents nitrogen or a —CR$^6$— grouping,
wherein $R^6$ represents hydrogen, fluorine, chlorine, bromine, methyl, ethyl, methoxy, ethoxy, propoxy, isopropoxy, methylthio, ethylthio, mehtylamino, ethylamino, dimethylamino or diethylamino,
and in which, furthermore, $R^3$ represents a radical $R^7$,
wherein $R^7$ represents $C_1$–$C_4$-alkyl [which is optionally substituted by fluorine and/or chlorine], or represents di-($C_1$–$C_2$-alkyl)-amino, or represents benzyl or phenyl [which are optionally substituted by fluorine, chlorine, bromine, cyano, nitro, $C_1$–$C_4$-alkyl, trifluoromethyl, $C_1$–$C_4$-alkoxy, trifluoromethoxy, difluoromethoxy, $C_1$–$C_4$-alkylthio, $C_1$–$C_4$-alkoxycarbonyl, $C_1$–$C_4$-alkylsulphinyl, $C_1$–$C_4$-alkylsulphonyl, dimethylaminosulphonyl, phenyl or phenoxy],
and in which, furthermore, $R^4$ represents the radical —O—$R^9$,
wherein $R^9$ represents $C_1$–$C_4$-alkyl [which is optionally substituted by fluorine or chlorine], or represents $C_3$–$C_6$-alkenyl [which is optionally substituted by chlorine], or represents $C_1$–$C_3$-alkoxy-carbonyl-$C_1$–$C_2$-alkyl, phenyl, phenylethyl or benzyl [which are optionally substituted by fluorine, chlorine, nitro, methyl, methoxy or $C_1$–$C_2$-alkoxy-carbonyl];
or in which, furthermore, $R^4$ represents the radical

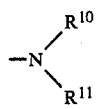

wherein $R^{10}$ represents hydrogen or methyl and $R^{11}$ represents hydrogen or $C_1$–$C_3$-alkyl [which is optionally substituted by fluorine, chlorine, cyano, $C_1$–$C_2$-alkoxy or $C_1$–$C_2$-alkoxy-carbonyl], or represents $C_3$–$C_6$-cycloalkyl, phenyl, benzyl or phenylethyl [which are optionally substituted by fluorine, chlorine, bromine, nitro, cyano, $C_1$–$C_2$-alkyl, $C_1$–$C_2$-alkoxy or $C_1$–$C_2$-alkoxy-carbonyl], or represents acetyl, methoxycarbonyl, benzenesulphonyl or toluenesulphonyl;
and in which, furthermore, M represents hydrogen or one equivalent of sodium, potassium or calcium, or represents the radical —COR$^7$,
wherein $R^7$ has the abovementioned particularly preferred meanings;
and (B) X, Y, Z, $R^1$, $R^2$, $R^4$ and M have the meanings given above under (A) and $R^3$ represents a radical —NHR$^8$,
wherein $R^8$ represents $C_1$–$C_4$-alkyl, cyclohexyl, benzyl, phenyl or phenylsulphonyl (the phenyl radicals optionally being substituted by fluorine, chlorine, $C_1$–$C_2$-alkyl, $C_1$–$C_2$-alkoxy, trifluoromethyl, trifluoromethoxy, chlorofluoromethoxy, chlorodifluoromethoxy, dichloromethoxy, 2-chloroethoxy, $C_1$–$C_2$-alkylthio, $C_1$–$C_2$-alkylsulphinyl, $C_1$–$C_2$-alkylsulphonyl, dimethylaminosulphonyl, N-methoxy-N-methylaminosulphonyl and/or $C_1$–$C_2$-alkoxycarbonyl).

The invention furthermore particularly relates to adducts of compounds of the formula (I)—as defined above—with hydrogen halide acids, such as hydrogen chloride, hydrogen bromide and hydrogen iodide, with sulphuric acid, with alkanesulphonic acids which have 1 to 4 carbon atoms and are optionally substituted by fluorine and/or chlorine, or with benzene- or naphthalenesulphonic acids which are optionally substituted by fluorine, chlorine, bromine or methyl.

If, for example, N'-(4,6-dimethoxy-pyrimidin-2-yl)N''-benzyloxy-N'''-(2-chloro-phenylmethylsulphonyl)-guanidine and trifluoroacetic anhydride are used as starting substances for process variant (a), the course of the reaction can be outlined by the following equation:

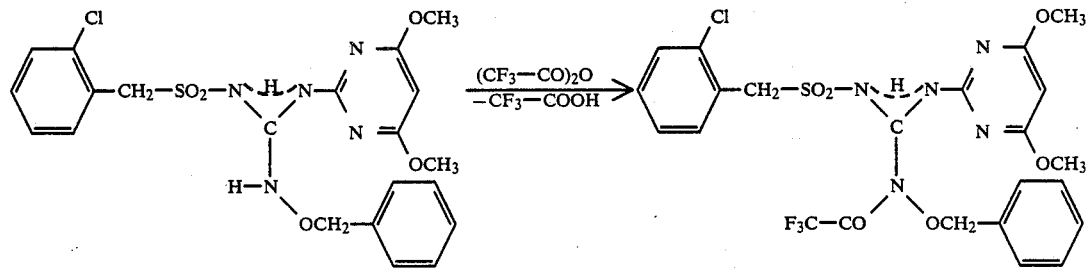

If, for example, N'-(4-ethoxy-6-methyl-s-triazin-2-yl)-N"-methoxy-N""-(2-ethoxycarbonyl-benzenesulphonyl)guanidine and 2-chloro-phenyl isocyanate are used as starting substances for process variant (b), the course of the reaction can be outlined by the following equation:

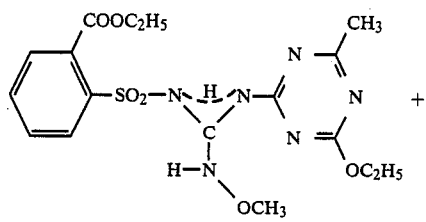

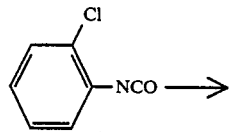

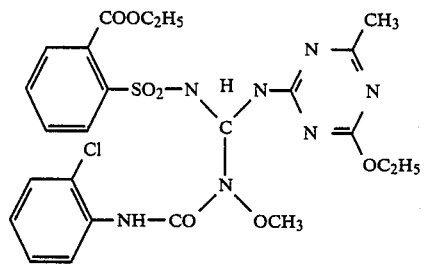

If, for example, N'-(4-methoxy-6-methyl-pyrimidin-2-yl)-N"-methoxy-N"-(4-fluoro-benzoyl)-guanidine and 2-methoxycarbonyl-benzenesulphonyl chloride are used as starting substances for process variant (c), the course of the reaction can be outlined by the following equation:

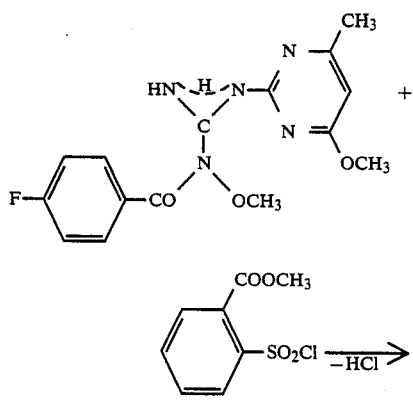

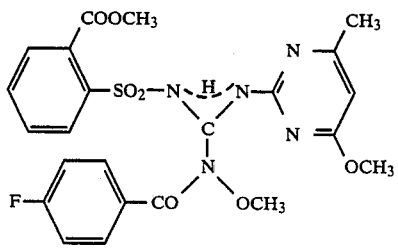

If, for example, N'-(4-methoxy-6-methyl-s-triazin-2-yl)-N"-isopropoxy-N"-methylcarbonyl-N""-(2-methoxycarbonyl-benzenesulphonyl)-guanidine and sodium methylate are used as starting substances for process variant (d), the course of the reaction can be outlined by the following equation:

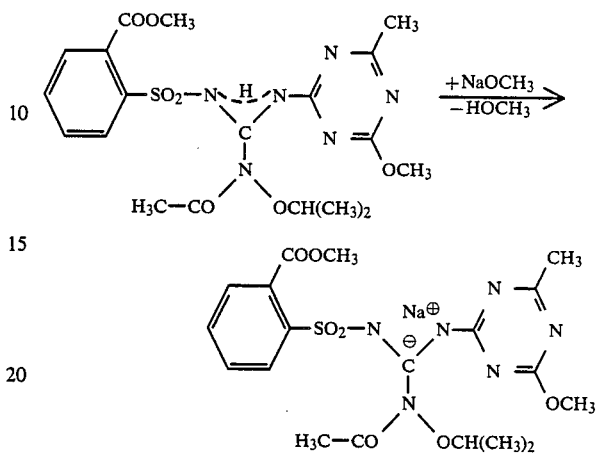

If, for example, N'-(4-difluoromethoxy-6-methyl-pyrimidin-2-yl)-N"-ethoxy-N"(1-chloro-1-ethyl)-carbonyl-N""-(2-chlorobenzenesulphonyl)-guanidine and methanesulphonic acid are used as starting substances for process variant (e), the course of the reaction can be outlined by the following equation:

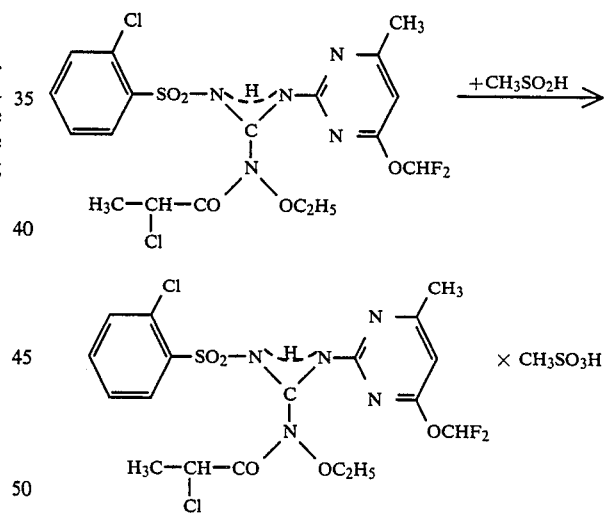

If, for example, N'-(4-methoxy-6-methyl-s-triazin-2-yl)-N"-isopropoxy-N"-ethylcarbonyl-N""-(2-methoxycarbonyl-benzenesulphonyl)-guanidine and acetylchloride are used as starting substances for process variant (f/α), the course of the reaction can be outlined by the following equation:

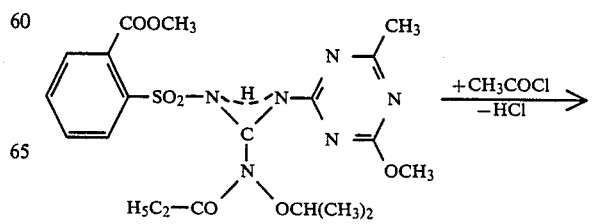

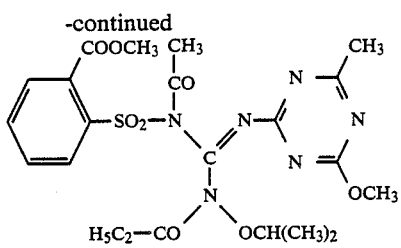

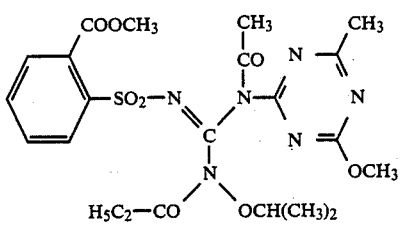

If, for example, N'-(4-methoxy-6-methyl-pyrimidin-2-yl)-N'''-methoxy-N''''-(2-methoxycarbonyl-benzenesulphonyl)-guanidine and at least twice the molar amount of acetyl chloride are used as starting substances for process variant (f/β), the course of the reaction can be outlined by the following equation:

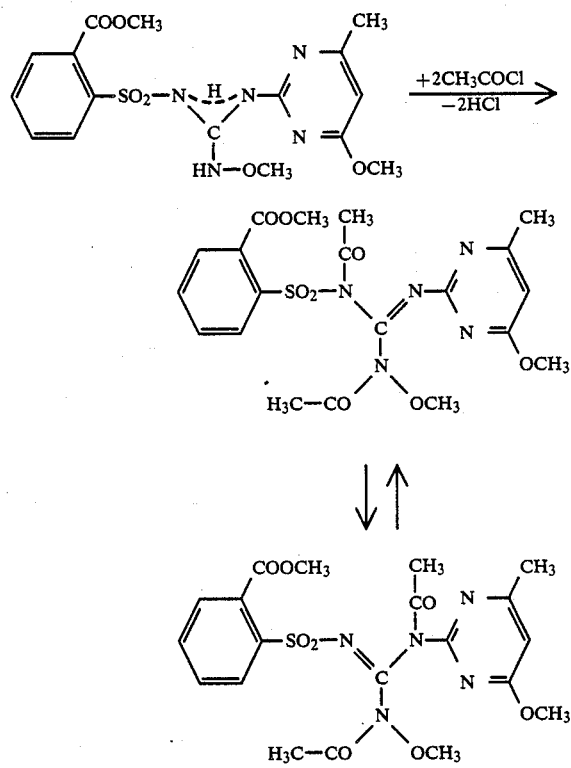

Formula (II) provides a general definition of the sulphonylguanidine derivatives to be used as starting substances in process variant (a). In formula (II), X, Y, Z, $R^1$, $R^2$ and $R^4$ preferably or in particular have the same meanings as are given as preferred or as particularly preferred above in the context of the substituent definition for formula (I).

Examples which may be mentioned of the compounds of the formula (II) are: N'-(4,6-dimethyl-pyrimidin-2-yl)-, N'-(4,6-dimethoxy-pyrimidin-2-yl)-, N'-(4-methoxy-6-methyl-pyrimidin-2-yl)-, N'-(4-ethoxy-6-methyl-pyrimidin-2-yl)-, N'-(4-methyl-pyrimidin-2-yl)-, N'-(4-chloro-6-methoxy-pyrimidin-2-yl)-, N'-(4-chloro-6-ethoxy-pyrimidin-2-yl)-, N'-(4-chloro-6-dimethylamino-pyrimidin-2-yl)-, N'-(4-methyl-6-methylthio-pyrimidin-2-yl)-, N'-(4-dimethylamino-6-methyl-pyrimidin-2-yl)-, N'-(4-difluoromethoxy-6-methyl-pyrimidin-2-yl)-, N'-(2,6-dimethyl-pyrimidin-4-yl)-, N'-(2,6-dimethoxy-pyrimidin-4-yl)-, N'-(4,6-dimethyl-s-triazin-2-yl)-, N'-(4-methoxy-6-methyl-s-triazin-2-yl)-, N'-(4-ethoxy-6-methyl-s-triazin-2-yl)-, N'-(4,6-dimethoxy-s-triazin-2-yl)-, N'-(4,6-diethoxy-s-triazin-2-yl)-, N'-(4-methyl-6-methoxy-s-triazin-2-yl)-, N'-(4-ethoxy-6-methoxy-s-triazin-2-yl)-, N'-(4-methyl-6-methylthio-s-triazin-2-yl)-, N'-(4-ethylthio-6-methyl-s-triazin-2-yl)-, N'(4-methoxy-6-methylthio-s-triazin-2-yl)-, N'-(4-ethoxy-6-methylthio-s-triazin-2-yl)-, N'-(4-ethylthio-6-methoxy-s-triazin-2-yl)-, N'-(4-ethoxy-6-ethylthio-s-triazin-2-yl)-, N'-(4,6-bis-methylthio-s-triazin-2-yl)-, N'-(4,6-bis-ethylthio-s-triazin-2-yl)-, N'-(4-methyl-6-methylamino-s-triazin-2-yl)-, N'-(4-ethylamino-6-methyl-s-triazin-2-yl)-, N'-(4-dimethylamino-6-methyl-s-triazin-2-yl)-, N'-(4-diethylamino-6-methyl-s-triazin-2-yl)-, N'-(4-methoxy-6-methylamino-s-triazin-2-yl)-, N'-(4-ethylamino-6-methoxy-s-triazin-2-yl)-, N'-(4-dimethylamino-6-methoxy-s-triazin-2-yl)-, N'-(4-diethylamino-6-methoxy-s-triazin-2-yl)-, N'-(4-ethoxy-6-methylamino-s-triazin-2-yl)-, N'-(4-ethoxy-6-ethylamino-s-triazin-2-yl)-, N'-(4-dimethylamino-6-ethoxy-s-triazin-2-yl)-, N'-(4-diethylamino-6-ethoxy-s-triazin-2-yl)-, N'-(4-methylamino-6-methylthio-s-triazin-2-yl)-, N'-(4-ethylamino-6-methylthio-s-triazin-2-yl)-, N'-(4-dimethylamino-6-methylthio-s-triazin-2-yl)-, N'-(4-diethylamino-6-methylthio-s-triazin-2-yl)-, N'-(4-ethylthio-6-methylamino-s-triazin-2-yl)-, N'-(4-dimethylamino-6-ethylthio-s-triazin-2-yl)-, N'-(4-diethylamino-6-ethylthio-s-triazin-2-yl)-, N'-(5,6-dimethyl-1,2,4-triazin-3-yl)-, N'-(5-methyl-1,2,4-triazin-3-yl)- and N'-(4,6-dimethyl-pyrid-2-yl)-N''-methoxy-, -N''-ethoxy-, -N''-propoxy-, -N''-isopropoxy-, -N''-butoxy-, -N''-isobutoxy-, -N''-s.-butoxy-, -N''-pentoxy-, -N''-hexyloxy-, -N''-octyloxy-, -N''-allyloxy-, -N''-crotyloxy-, -N''-(3-chloro-propoxy)-, -N''-methoxycarbonylmethoxy-, -N''-ethoxycarbonylmethoxy, -N''-(1-methoxycarbonylethoxy)-, -N''-(1-ethoxycarbonyl-ethoxy)-, -N''-(2-phenylethoxy)-, -N''-phenoxy-, -N''-benzyloxy-, -N''-(4-methyl-benzyloxy)-, N''-(4-fluoro-benzyloxy)-, -N''-(4-chloro-benzyloxy)-, -N''-(4-nitro-benzyloxy)-, -N''-(2,6-dichloro-benzyloxy)-, -N''-(4-methoxycarbonylbenzyloxy)- and -N''-(4-ethoxycarbonylbenzyloxy)-N'''-benzenesulphonyl-, -N'''-(2-chlorobenzenesulphonyl)-, -N'''-(3-chloro-benzenesulphonyl)-, -N'''-(4-chloro-benzenesulphonyl)-, -N'''-(2-fluoro-benzenesulphonyl)-, -N'''-(4-fluoro-benzenesulphonyl)-, -N'''-(2-bromo-benzenesulphonyl), -N'''-(4-bromobenzenesulphonyl)-, -N'''-(2-cyano-benzenesulphonyl)-, -N'''-(2-nitro-benzenesulphonyl)-, -N'''-(4-nitro-benzenesulphonyl)-, -N''''-(2-methyl-benzenesulphonyl)-N'''-(4-methyl-benzenesulphonyl)-, -N'''-(2-chloro-methylbenzenesulphonyl)-, -N'''-(2-trifluoromethyl-benzenesulphonyl)-, -N'''-(2-methoxy-benzenesulphonyl)-, -N'''-(4-methoxy-benzenesulphonyl)-, -N'''-(2-methylthio-benzenesulphonyl)-, -N'''-(2-difluoromethoxybenzenesulphonyl)-, -N'''-(2-trifluoromethoxy-benzenesulphonyl)-, -N'''-(2-methylthiomethylbenzenesulphonyl)-, -N'''-(2- dimethylaminosulphonylbenzenesulphonyl)-, -N'''-(2-phenyl-benzenesulphonyl)-, -N'''-(2-methoxysulphonyl-benzenesulphonyl)-, -N'''-(2-methoxycarbonyl-benzenesulphonyl)-, -N'''-(2-ethoxycarbonylbenzenesulphonyl)-, -N'''-(2-propoxycarbonyl-benzenesulphonyl)-, -N'''-(2-methylaminocarbonylbenzenesulphonyl)-, -N'''-(2-ethylaminocarbonyl-benzenesulphonyl)-, -N'''-(2-propylaminocarbonyl-benzenesulphonyl)-, -N'''-(2-methoxyaminocarbonyl-benzenesulphonyl)-, -N'''-(2-ethoxyaminocarbonyl-benzenesulphonyl)-, -N'''-(2-propoxyaminocarbonyl-benzenesulphonyl)-, -N'''-(2-dimethylaminocarbonylbenzenesulphonyl)-, -N'''-(2-diethylaminocarbonyl-benzenesulphonyl)-, and -N'''-(2-methoxyaminosulphonyl-benzenesulphonyl)-guanidine.

The compounds of the formula (II) are known and/or can be prepared by known processes (compare, for example, European Patent A-121,082).

Formula (III) provides a general definition of the acylating agents also to be used as starting substances in process (a) according to the invention. In this formula (III), $R^7$ preferably represents those radicals which have already been mentioned as preferred for these substituents in connection with the description of the substances of the formula (I) according to the invention. W in this formula preferably represents halogen, such as fluorine, chlorine or bromine, or represents the radical $R^7COO-$.

Examples which may be mentioned of the compounds of the formula (III) are:

$$R^7COW \qquad (III)$$

W=fluorine, chlorine, bromine or $R^7COO-$

TABLE 1

| $R^7$ | $R^7$ | $R^7$ |
|---|---|---|
| $CH_3$ | $CH_3-CH(Cl)-$ | 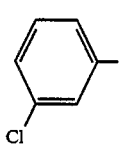 Br— |
| $C_2H_5$ | $ClCH_2-$ | 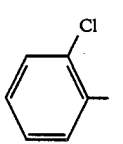 F— |
| $n-C_3H_7$ | $CH_3O-CH_2-$ | 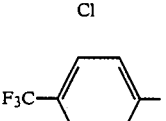 Br |
| $i-C_3H_7$ | 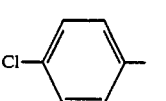 | 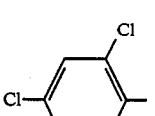 F |
| $n-C_4H_9$ |  —$CH_2-$ |  Cl |

TABLE 1-continued

| $R^7$ | $R^7$ | $R^7$ |
|---|---|---|
| $i-C_4H_9$ | 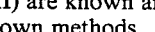 F | 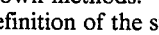 F,F |
| $s-C_4H_9$ | 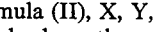 Cl | 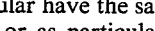 F,Cl |
| $t-C_4H_9$ | Cl—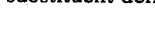 | $F_3C-$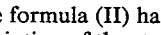 |
| $CF_3-$ | $O_2N-$ | Cl—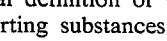—Cl |
| $CHCl_2-$ | 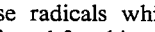 Cl,Cl | NC—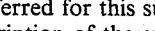 |
| $CCl_3-$ | | |

The compounds of the formula (III) are known and/or can be prepared by generally known methods.

Formula (II) provides a general definition of the sulphonylguanidine derivatives to be used as starting substances in process variant (b). In formula (II), X, Y, Z, $R^1$, $R^2$ and $R^4$ preferably or in particular have the same meanings as are given as preferred or as particularly preferred above in the context of the substituent definition for formula (I).

Examples of the compounds of the formula (II) have already been given above in the description of the starting substances for process (a).

Formula (IV) provides a general definition of the isocyanates also to be used as starting substances in process (b) according to the invention. In this formula (IV), $R^8$ preferably represents those radicals which have already been mentioned as preferred for this substituent in connection with the description of the substances of the formula (I) according to the invention.

Examples which may be mentioned of the compounds of the formula (IV) are:

$$R^8-NCO \qquad (IV)$$

TABLE 2

| $R^8$ | $R^8$ | $R^8$ |
|---|---|---|
| $CH_3-$ |  | Br— |
| $C_2H_5-$ | —$CH_2-$ | F— |

TABLE 2-continued

| R⁸ | R⁸ | R⁸ |
|---|---|---|
| n-C₃H₇— | 2-F-phenyl | 2-Br-phenyl |
| (CH₃)₂CH— | 2-Cl-phenyl | 3-F-phenyl |
| 2-CH₃-phenyl | 4-Cl-phenyl | 3-Cl-phenyl |
| 3-CF₃-phenyl | 4-O₂N-phenyl | 2-(COOCH₃)-phenyl-SO₂— |
| 2-Cl-phenyl-SO₂— | 2,4-Cl₂-phenyl | 2-Br-phenyl-SO₂— |
| cyclohexyl | 2,4-Cl₂-phenyl (isomer) | 2-NO₂-phenyl |
| 4-CH₃-phenyl | 3-Cl-4-CH₃-phenyl | 3-Cl-4-CF₃-phenyl |
| 4-H₃C-phenyl-SO₂— | | |

The compounds of the formula (IV) are generally known compounds of organic chemistry.

Formula (V) provides a general definition of the guanidine derivatives to be used as starting substances in process variant (c). In formula (V), X, Y, Z, R², R³ and R⁴ preferably or in particular have the same meanings as are given as preferred or as particularly preferred above in the context of the substituent definition for formula (I).

Examples which may be mentioned of starting substances of the formula (V) are: N'-(2,6-dimethoxy-pyrimidin-4-yl)-, N'-(2,6-dimethyl-pyrimidin-4-yl)-, N'-(4,6-dimethyl-pyrimidin-2-yl)-, N'-(4-methyl-pyrimidin-2-yl)-, N'-(4-ethyl-pyrimidin-2yl)-, N'-(4-methoxy-6-methyl-pyrimidin-2-yl)-, N'-(4-ethoxy-6-methyl-pyrimidin-2-yl)-, N'-(4-propoxy-6-methyl-2-yl)-, N'-(4-isopropoxy-6-methyl-pyrimidin-2-yl)-, N'-(4-chloro-6-methoxy-pyrimidin-2-yl)-, N'-(4-chloro-6-ethoxy-pyrimidin-2-yl)-, N'-(4-chloro-6-dimethylamino-pyrimidin-2-yl)-, N'-(4-methyl-6-methylthio-pyrimidin-2-yl)-, N'-(4,6-dimethoxy-pyrimidin-2-yl)-, N'-(4-difluoromethoxy-6-methyl-pyrimidin-2-yl)-, N'-(4-dimethylamino-6-methyl-pyrimidin-2-yl)-, N'-(4,6-dimethyl-s-triazin-2-yl)-, N'-(4-methoxy-6-methyl-s-triazin-2-yl)-, N'-(4-ethoxy-6-methyl-s-triazin-2-yl)-, N'-(4,6-dimethoxy-s-triazin-2-yl)-, N'-(4,6-diethoxy-s-triazin-2-yl)-, N'-(4-ethoxy-6-methoxy-s-triazin-2-yl)-, N'-(4-methyl-6-methylthio-s-triazin-2-yl)-, N'-(4-ehylthio-6-methyl-s-triazin-2-yl)-, N'(4-methoxy-6-methylthio-s-triazin-2-yl)-, N'-(4-ethoxy-6-methylthio-s-triazin-2-yl)-, N'-(4-ethylthio-6-methoxy-s-triazin-2-yl)-, N'-(4-ethoxy-6-ethylthio-s-triazin-2-yl)-, N'-(4,6-bis-methylthio-s-triazin-2-yl)-, N'-4,6-(bis-ethylthio-s-triazin-2-yl)-, N'-(4-methyl-6-methylamino-s-triazin-2-yl)-, N'-(4-ethylamino-6-methyl-s-triazin-2-yl)-, N'-(4-dimethylamino-6-methyl-s-triazin-2-yl)-, N'-(4-diethylamino-6-methyl-s-triazin-2-yl)-, N'-(4-methoxy-6-methylamino-s-triazin-2-yl)-, N'-(4-ethylamino-6-methoxy-s-triazin-2-yl)-, N'-(4-dimethylamino-6-methoxy-s-triazin-2-yl)-, N'-(4-diethylamino-6-methoxy-s-triazin-2-yl), N'-(4-ethoxy-6-methylamino-s-triazin-2-yl)-, N'-(4-ethoxy-6-ethylamino-s-triazin-2-yl)-, N'-(4-dimethylamino-6-ethoxy-s-triazin-2-yl)-, N'-(4-diethylamino-6-ethoxy-s-triazin-2-yl)-, N'-(4-methylamino-6-methylthio-s-triazin-2-yl)-, N'-(4-ethylamino-6-methylthio-s-triazin-2-yl)-, N'-(4-dimethylamino-6-methylthio-s-triazin-2-yl)-, N'-(4-diethylamino-6-methylthio-s-triazin-2-yl)-, N'-(4-ethylthio-6-methylamino-s-triazin-2-yl)-, N'-(4-dimethylamino-6-ethylthio-s-triazin-2-yl)-, N'-(4-diethylamino-6-ethylthio-s-triazin-2-yl)-, N'-(5,6-dimethyl-1,2,4-triazin-3-yl)-, N'-(5-methyl-1,2,4-triazin-3-yl)- and N'-(4,6-dimethyl-pyrid-2-yl)-N''-methylcarbonyl-, -N''-methylaminocarbonyl-, -N''-phenylcarbonyl-, -N''-phenylaminocarbonyl-, -N''-(4-chloro-phenyl)-carbonyl-, -N''-(4-chloro-phenyl)-aminocarbonyl-, -N''-(4-fluoro-phenyl)-carbonyl-, -N''-(4-fluoro-phenyl)-aminocarbonyl-, -N''-(4-bromo-phenyl)-carbonyl-, -N''-(4-bromo-phenyl)-aminocarbonyl-, -N''-ethylcarbonyl-, -N''-n-propylcarbonyl-, -N''-i-propylcarbonyl-, -N''-n-butylcarbonyl-, -N''-i-butylcarbonyl-, -N''-sec.-butylcarbonyl-, -N''-tert.-butylcarbonyl-, -N''-trifluoromethylcarbonyl-, -N''-dichloromethylcarbonyl-, -N''-trichloromethylcarbonyl-, -N''-(1-chloro-1-ethyl)-carbonyl, -N''-(3-chloro-phenyl)-carbonyl-, -N''-(3-chloro-phenyl)-aminocarbonyl-, -N''-(4-nitro-phenyl)-carbonyl-, -N''-benzylcarbonyl-, -N''-benzylaminocarbonyl-, -N''-(4-methyl-phenylsulphonyl)-aminocarbonyl-, -N''-(2-chloro-phenyl)-carbonyl-, -N''-(2-chloro-phenyl)-aminocarbonyl-, -N''-(2,4-dichloro-phenyl)-carbonyl-, -N''-(2,4-dichloro-phenyl)-aminocarbonyl-, -N''-(2-fluoro-phenyl)-carbonyl-, -N''-(2-fluoro-phenyl)-aminocarbonyl-, -N''-(3-fluoro-phenyl)-carbonyl-, -N''-(3-fluoro-phenyl)-aminocarbonyl-, -N''-(3-bromo-phenyl)-carbonyl, -N''-(3-bromo-phenyl)-aminocarbonyl-, -N''-(2-bromo-phenyl)-carbonyl-, -N''-(2-bromo-phenyl)-aminocarbonyl-, -N''-cyclohexylaminocarbonyl-, -N''-(3,4-dichloro-phenyl)-aminocarbonyl-, -N''-isopropylaminocarbonyl-, -N''-(2-nitro-phenyl)-aminocarbonyl-, -N''-(4-nitro-phenyl)-aminocarbonyl- and -N''-(3-trifluoro-phenyl)-aminocarbonyl-N''-methoxy-guanidine, -N''-ethoxy-guanidine, -N''-propoxy-guanidine, -N''-isopropoxy-guanidine, -N''-butoxy-guanidine, -N''-isobutoxy-guanidine, -N''-sec.-butoxy-guanidine, -N''-pentoxy-guanidine, -N''-isopentoxy-guanidine, -N''-hexyloxy-guanidine, -N''-octyloxy-guanidine, -N''-allyloxy-guanidine, -N''-(2-chloro-ethoxy)-guanidine, -N''-(2-fluoro-ethoxy)-guanidine, -N''-(2-chloro-propoxy)-guanidine, -N''-(2-fluoro-propoxy)-guanidine, -N''-(3-chloro-propoxy)-guanidine, -N''-(4-chloro-butoxy)-guanidine, -N''-methoxycarbonylmethoxy-guanidine, -N''-ethoxycarbonylmethoxy-guanidine, -N''-(1-methoxy-carbonylethoxy)-guanidine, -N''-(1-ethoxycarbonyl-ethoxy)-guanidine, -N''-dimethylaminocarbonylmethoxy-guanidine, -N''-(2-phenyl-ethoxy)-guanidine, -N''-phenoxy-guanidine, -N''-(4-methylbenzyloxy)-guanidine, -N''-(4-fluorobenzyloxy)-guanidine, -N"-(4-chloro-benzyloxy)-guanidine, -N"-(4-nitro-benzyloxy)-guanidine, -N"-(2,6-dichloro-benzyloxy)-guanidine, -N"-(4-methoxy-carbonylbenzyloxy)-guanidine and -N"-(4-ethoxycarbonyl-benzyloxy)-guanidine.

The guanidine derivatives of the formula (V) to be used as starting substances are new. The guanidine derivatives of the formula (V) are obtained by a process in which guanidines of the formula (VII)

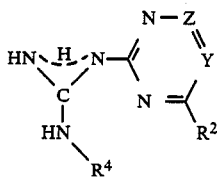  (VII)

in which
X, Y, Z, R² and R⁴ have the abovementioned meanings,
(a) in the case where R³ represents the radical R⁷, are reacted with acylating agents of the formula (III)

R⁷COW      (III)

in which
R⁷ and W have the abovementioned meanings,
if appropriate in the presence of acid acceptors, such as, for example, 1,4-diazabicyclo-[2,2,0]-octane and pyridine, and if appropriate in the presence of inert diluents, such as, for example, methylene chloride, chloroform and dioxane, at temperatures between −20° C. and +100° C., preferably between −5° C. and +80° C. (the reaction products of the formula (V) can be worked up in the customary manner);
or
(b) in the case where R³ represents the radical —NHR⁸, are reacted with isocyanates of the formula (IV)

R⁸—NCO      (IV)

in which
R⁸ has the abovementioned meanings,
if appropriate in the presence of catalysts, such as, for example, organic tin compounds, such as dibutyl-tin dilaurate, or tertiary amines, such as, for example, triethylamine and 1,4-diazabicyclo-[2,2,2]-octane, and if appropriate in the presence of inert diluents, such as, for example, toluene, dioxane, dimethylformamide and acetonitrile, at temperatures between 0° C. and 140° C., preferably between 10° C. and 120° C. The reaction products of the formula (V) can be worked up in the customary manner.

The guanidines of the formula (VII) are known and/or can be prepared by known methods (compare, for example, European Patent A-121,082). The starting substances of the formulae (III) and (IV) are known compounds of organic chemistry.

Formula (VI) provides a general definition of the sulphonyl chlorides furthermore to be used for process (c). In formula (VI), R¹ preferably or in particular has the same meanings as are given as preferred or as particularly preferred above in the context of the substituent definition for formula (I).

Examples which may be mentioned of starting substances of the formula (VI) are: 2-chloro-, 3-chloro-, 4-chloro-, 2,5-dichloro-, 2-fluoro-, 4-fluoro-, 2-bromo-, 4-bromo-, 2-nitro-, 4-nitro-, 2-cyano-, 2-methyl-,4-methyl-, 2-chloromethyl-, 2-trifluoromethyl-, 2-methoxy-, 2-difluoromethoxy-, 2-trifluoromethoxy-, 2-methylthio-, 2-methylthiomethyl-, 2-methylsulphinylmethyl-, 2-methylsulphonylmethyl-, 2-dimethylaminoisulphonyl-, 2-diethylaminosulphonyl-, 2-phenyl-, 2-methoxycarbonyl-, 2-ethoxycarbonyl-, 2-propoxycarbonyl-, 2-isopropoxycarbonyl-, 2-butoxycarbonyl-, 2-dimethylaminocarbonyl-, 2-diethylaminocarbonyl-, 2-phenoxy-, 2-methyl-5-chloro-, 2-chloro-5-trifluoromethyl-, 2-methylsulphonyl-, 2-ethylsulphonyl-, 2-chloro-4-trifluoromethoxy-, 3-chloro-4-trifluoromethoxy-, 2-trifluoromethoxy-5-chloro- and 3,5-dichlorobenzenesulphonyl chloride, (2-chloro-phenyl)-, (2-cyano-phenyl)- and (2-methoxy-carbonyl-phenyl)-methanesulphonyl chloride; and furthermore methane-, chloromethane-, trifluoromethane-, ethane-, 2-chloroethane-, ethene-, propane-, butane-, perfluorobutane- and perfluorooctane-sulphonyl chloride.

The sulphonyl chlorides of the formula (VI) are known and/or can be prepared by processes which are known per se (compare J. Org. Chem. 33 (1968), 2104; J. Org. Chem. 25 (1960), 1824; DE-AS (German Published Specification) 2,308,262; EP-OS (European Published Specifications) 23,140, 23,141, 23,422, 35,893, 48,143, 51,466, 64,322, 70,041, 44,808 and 44,809; U.S. Pat. Nos. 2,929,820, 4,282,242, 4,348,220 and 4,372,778 and Angew. Chem. 93 (1981), 151).

Formula (I)—with the proviso that M represents hydrogen—provides a general definition of the compounds to be used as starting substances in process variant (d). In formula (I)—where this relates to the compounds to be used as starting substances for process (d)—M represents hydrogen and X, Y, Z, R¹, R², R³ and R⁴ preferably or in particular have the same meanings as are given as preferred or as particularly preferred above in the context of the substituent definition for formula (I).

The compounds of the formula (I) to be used as starting substances for process (d) can be prepared by the processes described under (a), (b) and (c).

Examples which may be mentioned of the metal hydroxides, hydrides or alkanolates or organometallic compounds to be used in process (d) are: lithium hydroxide, sodium hydroxide, potassium hydroxide, magnesium hydroxide and calcium hydroxide, lithium hydride, sodium hydride and calcium hydride, sodium methanolate and ethanolate, potassium methanolate and ethanolate and potassium tert.-butanolate, as well as butyl-lithium and isopropylmagnesium chloride.

Formula (I)—with the proviso that M represents hydrogen—provides a general definition of the compounds to be used as starting substances in process variant (e). In formula (I)—where this relates to the compounds to be used as starting substances for process (e)-M represents hydrogen and X, Y, Z, R¹, R², R³ and R⁴ preferably or in particular have the same meanings as are given as preferred or as particularly preferred above in the context of the substituent definition for formula (I).

The compounds of the formula (I) to be used as starting substances for process (e) can be prepared by the processes described under (a), (b) and (c).

Strong acids are used as starting substances in process (e). These are preferably hydrogen halide acids, such as hydrogen chloride, hydrogen bromide or hydrogen iodide, and furthermore sulphuric acid or alkanesulphonic acids which have up to 4 carbon atoms and are optionally substituted by fluorine or chlorine, such as, for example, methanesulphonic acid, ethanesulphonic acid, chloromethanesulphonic acid, 2-chloroethanesulphonic acid and trifluoromethanesulphonic acid, trifluoroacetic acid, and furthermore benzenesulphonic acid, p-toluenesulphonic acid, naphthalene-1-sulphonic acid, naphthalene-2-sulphonic acid and naphthalene-1,4-, -1,5-, -1,6-, -2,6- and -2,7-disulphonic acid.

Formula (I)—with the proviso that M represents hydrogen—provides a general definition of the compounds to be used as starting substances in process variant (f-α). In formula (I)—where this relates to the compounds to be used as starting substances for process (f-α)-M represents hydrogen and X, Y, Z, $R^1$, $R^2$, $R^3$ and $R^4$ preferably or in particular have the same meanings as are given as preferred or as particularly preferred above in the context of the substituent definition for formula (I).

The compounds of the formula (I) to be used as starting substances for process (f-α) can be prepared by the processes described under (a), (b) and (c).

Formula (II) provides a general definition of the sulphonylguanidine derivatives to be used as starting substances in process (f-β) according to the invention. In this formula (II), X, Y, Z, $R^1$, $R^2$ and $R^4$ preferably represent those radicals which have already been mentioned as preferred for these substituents in connection with the description of the substances of the formula (I) according to the invention.

Examples of the sulphonylguanidine derivatives of the formula (II) and their preparation processes have already been given above in connection with the description of the starting substances for process (a).

Formula (III) provides a general definition of the acylating agents also to be used as starting substances in process variants (f-α) and (f-β). In formula (III), $R^7$ preferably or in particular has the same meaning as is given as preferred or as particularly preferred above in the context of the substituent definition for formula (I). W in this formula preferably represents halogen, such as fluorine, chlorine or bromine, or represents the radical $R^7COO-$.

Examples of the acylating agents of the formula (III) and their preparation processes have already been given above in connection with the description of the starting substances for process (a).

Process (a) according to the invention for the preparation of the new acylated sulphonylguanidines of the formula (I) is preferably carried out using diluents. Possible diluents here are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as dimethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and dimethylsulphoxide, tetramethylene sulphone, pyridine and 2-methyl-5-ethylpyridine.

Acid acceptors which can be used in process (a) according to the invention are all the acid-binding agents which can usually be employed for such reactions. Acid-binding agents which are preferably suitable are alkali metal hydroxides, such as, for example, sodium hydroxide and potassium hydroxide, alkaline earth metal hydroxides, such as, for example, calcium hydroxide, alkali metal carbonates and alcoholates, such as sodium carbonate and potassium carbonate, sodium methylate and ethylate and potassium methylate and ethylate, and furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU), 1,4-diazabicyclo-[2,2,2]-octane (DABCO), 2-methyl-5-ethylpyridine and 4-dimethylaminopyridine.

The reaction temperatures can be varied within a substantial range in process (a) according to the invention. The reaction is in general carried out at temperatures between $-20°$ C. and $+120°$ C., preferably at temperatures between $-10°$ C. and $+100°$ C.

Process (a) according to the invention is in general carried out under normal pressure. However, it is also possible for it to be carried out under increased or reduced pressure.

For carrying out process (a) according to the invention, the particular starting substances required are in general employed in approximately equimolar amounts. The reactions are in general carried out in a suitable diluent in the presence of an acid acceptor, and the reaction mixture is stirred for several hours at the particular temperature required. Working up in process (a) according to the invention is in each case by customary methods. After distilling off volatile components, if appropriate, the mixture is washed with water, dried, filtered and concentrated. The products of the formula (I) which remain in the residue are crystallized by digestion with organic solvents, such as, for example, diethyl ether, ethyl acetate, ethanol or isopropanol, and if appropriate purified by recrystallization.

Process (b) according to the invention is preferably carried out using diluents. Possible diluents are virtually all the inert organic solvents, but preferably aprotic polar solvents, such as have been mentioned above in connection with the description of process (a) according to the invention.

Preferred catalysts which can be used for the reaction according to process variant (b) are tertiary amines, such as triethylamine and 1,4-diazabicyclo-[2,2,2]-octane, and organic tin compounds, such as, for example, dibutyl-tin dilaurate. However, the addition of such catalysts is not essential.

The reaction temperatures can be varied within a substantial range in process (b) according to the invention. The reaction is in general carried out at temperatures between $0°$ C. and $140°$ C., preferably at temperatures between $0°$ C. and $120°$ C.

Process (b) according to the invention is in general carried out under normal pressure. However, it is also possible for it to be carried out under increased or reduced pressure.

For carrying out process (b) according to the invention, the particular starting substances required are in general employed in approximately equimolar amounts. However, it is also possible for one of the two particular components employed to be used in a larger excess. The reactions are in general carried out in a suitable diluent in the presence of a catalyst, and the reaction mixture is stirred for several hours at the particular temperature required. Working up in process (b) according to the invention is in each case by customary methods. If the products of the formula (I) are obtained as crystals from the reaction mixture, they can be isolated by filtration with suction. Otherwise—if appropriate after concentration—the mixture is diluted with water and extracted with a solvent which is virtually immiscible with water, such as, for example, methylene chloride. The products of the formula (I) can be obtained in a pure form by washing the extraction solution with water, drying, filtering, concentrating the filtrate and recrystallizing the residue.

Process (c) according to the invention is preferably carried out using diluents. Possible diluents are virtually all the inert organic solvents, but preferably aprotic polar solvents, such as have been mentioned above in connection with the description of process (a) according to the invention.

Virtually all the acid-binding agents usually employed can be used as acid acceptors in process C. These include, in particular, the acid-binding agents mentioned above in connection with the description of process (a) according to the invention.

The reaction temperatures can be varied within a substantial range in process (c). The reaction is in general carried out between $-80°$ C. and $+100°$ C., preferably between $-30°$ C. and $+50°$ C. Process (c) is in general carried out under normal pressure.

For carrying out process (c) according to the invention, the particular starting substances required are in general employed in approximately equimolar amounts. However, it is also possible for one of the two particular components employed to be used in a smaller excess.

Process (c) can be carried out and working up can be effected analogously to process (a).

Process (d) according to the invention is preferably carried out using diluents. Possible diluents are virtually all the inert organic solvents. These include, in particular, alcohols, such as, for example, ethanol and n- and iso-propanol, ethers, such as, for example, tetrahydrofuran, dioxane and 1,2-dimethoxyethane, esters, such as, for example, ethyl acetate and methyl acetate, and nitriles, such as, for example, acetonitrile.

The reaction temperatures can be varied within a substantial range in process (d). The reaction is in general carried out between $-20°$ C. and $+50°$ C., preferably between $0°$ C. and $+30°$ C. Process (d) is in general carried out under normal pressure.

For carrying out process (d) according to the invention, in general between 0.9 and 1.2 mols, preferably between 0.95 and 1.1 mols, of metal compound are employed per mol of compound of the formula (I).

In general, the compounds of the formula (I) and the diluent are taken and—if appropriate with gentle external cooling—the metal compound—if appropriate dissolved in a diluent—is metered in. The reaction mixture is stirred until the reaction has ended. The salt-like products of the formula (I) are in general obtained as crystals and can be isolated by filtration with suction.

Process (e) according to the invention is preferably carried out using diluents. Possible diluents are virtually all the inert organic solvents. These include, in particular, alcohols, such as, for example, methanol, ethanol and n- and iso-propanol, ethers, such as, for example, tetrahydrofuran, dioxane and 1,2-dimethoxyethane, esters, such as, for example, methyl acetate and ethyl acetate, and ketones, such as acetone, methyl ethyl ketone and methyl isobutyl ketone.

If the acids used as starting substances are employed in aqueous solution, it may also be advantageous to use acetic anhydride as the diluent.

The reaction temperatures can be varied within a substantial range in process (e). The reaction is in general carried out between $-20°$ C. and $+50°$ C., preferably between $0°$ C. and $+30°$ C. Process (e) is in general carried out under normal pressure.

For carrying out process (e) according to the invention, in general between 1 and 10 mols, preferably between 1 and 5 mols, of a strong acid are employed per mol of compound of the formula (I).

In general, the compounds of the formula (I) and the diluent are taken and—if appropriate with gentle external cooling—the strong acid is metered in. The reaction mixture is stirred until the reaction has ended. The 1:1 adducts are in general obtained in the form of crystals and can be isolated by filtration with suction.

Process (f/α) according to the invention is preferably carried out using diluents. Possible diluents are virtually all the inert organic solvents, but preferably aprotic polar solvents, such as have been mentioned above in connection with the description of process (a) according to the invention.

Virtually all the acid-binding agents usually employed can be used as acid acceptors in process (f/α). These include, in particular, the acid-binding agents mentioned above in connection with the description of process (a) according to the invention.

The reaction temperatures can be varied within a substantial range in process (f/α). The reaction is in general carried out between $-20°$ C. and $+120°$ C., preferably between $-10°$ C. and $+100°$ C. Process (f/α) is in general carried out under normal pressure.

For carrying out process (f/α) according to the invention, the particular starting substances required are in general employed in approximately equimolar amounts. However, it is also possible to use one of the two particular components employed in a larger excess. The reactions are in general carried out in a suitable diluent in the presence of an acid acceptor, and the reaction mixture is stirred at the particular required temperature for several hours. Working up in process (f/α) according to the invention is in each case carried out by customary methods.

Process (f/β) according to the invention is preferably carried out using diluents. Possible diluents are virtually all the inert organic solvents, but preferably aprotic polar solvents, such as have been mentioned above in connection with the description of process (a) according to the invention.

Virtually all the acid-binding agents which are usually employed can be used as acid acceptors in process (f/β). These include, in particular, the acid-binding agents mentioned above in connection with the description of process (a) according to the invention.

The reaction temperatures can be varied within a substantial range in process (f/β). The reaction is in general carried out between $-20°$ C. and $+120°$ C., preferably between $-10°$ C. and $+100°$ C. Process (f/β) is in general carried out under normal pressure.

For carrying out process (f/β) according to the invention, in general between 2 and 5, preferably between 2.5 and 4.0 mols of acylating agent of the formula (III) and between 2 and 5, preferably between 2.5 and 4.0 mols of acid acceptor are employed per mol of sulphonylguanidine derivative of the formula (II).

Process (f/β) can be carried out and working up can be effected analogously to process (a).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings, and hopfields, and for the selective combating of weeds in annual cultures.

The compounds of the formula (I) according to the invention are suitable for combating monocotyledon and dicotyledon weeds by the pre- and post-emergence method. They exhibit a good crop plant tolerance for wheat, for example, especially when used by the post-emergence method.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polar substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, N-(2-benzothiazolyl)-N,N'-dimethyl-urea, 3-(3-chloro-4-methylphenyl)-1,1-dimethylurea, 3-(4-isopropylphenyl)-1,1-dimethylurea, 2-chloro-4-ethylamino-6-(1-methylethyl)-1,3,5-triazine, 2-chloro-4,6-diethylamino-1,3,5-triazine, 2-ethylamino-6-(1,1-dimethylethyl-amino)-4-methylthio-1,3,5-triazine, 4-amino-6-(1,1-dimethylethyl)-3-methylthio-1,2,4-triazin-5(4H)-one, 4-amino-6-(1,1-dimethylethyl)-3-ethylthio-1,2,4triazin-5(4H)-one, methyl 2-[4,5-dihydro-4-methyl-4-(1-methylethyl)-5-oxo-1H-imidazol-2-yl]-4(5)-methyl-benzoate, N-phosphonomethyl-glycine derivatives, 2-amino-4-(hydroxymethylphosphinyl)-butanoic acid, bis-(1-methyl-4-pyridinium) dichloride, methyl 3-(2,4-dichloro-phenoxy)-6-nitrobenzoate, methyl 2-[4-(2,4-dichlorophenoxy)-phenoxy]propionate, the R enantiomer of (trimethylsilyl)-methyl 2-{4-[(3,5-dichloro-2-pyridinyl)oxy]-phenoxy}-propionate, 2,4-dichlorophenoxyacetic acid, 2-(2,4-dichlorophenoxy)propionic acid, 4-chloro-2-methyl-phenoxy-acetic acid, 2-(4-chloro-2-methyl-phenoxy)-propionic acid, 3,5-diiodo-4-hydroxy-benzonitrile, 3,5-dibromo-4-hydroxy-benzonitrile and 3-isopropyl-2,1,3-benzo-thiadiazin-4-one 2,2-dioxide. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

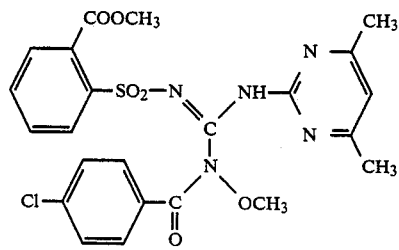

(Process (a))

A solution of 1.8 g (0.01 mol) of 4-chloro-benzoyl chloride in 15 ml of methylene chloride is added to a mixture of 3.9 g (0.01 mol) of N'-(4,6-dimethyl-pyrimidin-2-yl)-N'''-methoxy-N'''-(2-methoxycarbonyl-benzenesulphonyl)guanidine, 1.2 g (0.01 mol) of 1,4-diazabicyclo-[2,2,2]octane (DABCO) and 20 ml of methylene chloride, while stirring. The reaction mixture is stirred at 20° C. for 8 hours, washed with water, dried with sodium sulphate and filtered. The filtrate is concentrated and the residue is made to crystallize by trituration with diethyl ether.

2.1 g (40% of theory) of N'-(4,6-dimethyl-pyrimidin-2-yl)-N'''-methoxy-N''-(4-chloro-benzoyl)-N''''-(2-methoxycarbonyl-benzenesulphonyl)-guanidine of melting point 132° C. are obtained.

Example 2

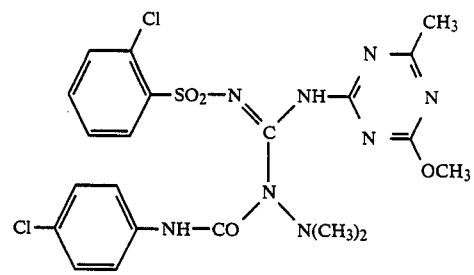

(Process (b))

A mixture of 2.1 g (0.005 mol) of N'-(4-methoxy-6-methyl-s-triazin-2-yl)-N''-dimethylamino-N'''-(2-chlorobenzenesulphonyl)-guanidine, 0.9 g (0.005 mol) of 4-chloro-phenyl isocyanate, 0.1 g of dibutyl-tin laurate and 20 ml of dioxane is stirred at 20° C. for 60 hours. The product obtained as crystals is then isolated by filtration with suction.

1.8 g (67% of theory) of N'-(4-methoxy-6-methyl-s-triazin-2-yl)-N''-dimethylamino-N''-(4-chloro-phenylamino-carbonyl)-N''''-(2-chloro-benzene-sulphonyl)-guanidine of melting point 174° C. are obtained.

Example 3

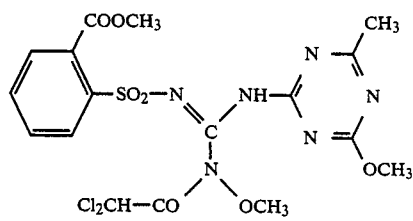

(Process (c))

7.5 g (0.032 mol) of methyl 2-chlorosulphonylbenzoate are added to a mixture, cooled to −10° C., of 9.0 g (0.028 mol) of N'-(4-methoxy-6-methyl-s-triazin-2-yl)-N''-methoxy-N''-dichloroacetyl-guanidine and 100 ml of methylene chloride. 3.5 g (0.032 mol) of 1,4-diazabicyclo[2,2,2]-octane are then added to this mixture, cooled to −10° C., while stirring. After the mixture has been stirred at 20° C., for 15 hours, it is washed with water, dried with sodium sulphate, filtered and concentrated carefully under reduced pressure.

12.9 g (89% of theory) of N'-(4-methoxy-6-methyl-s-triazin-2-yl)-N''-methoxy-N''-dichloroacetyl-N'''-(2-methoxycarbonyl-benzenesulphonyl)-guanidine are obtained as an oil of refractive index $n_D^{20} = 1.5722$.

Example 4

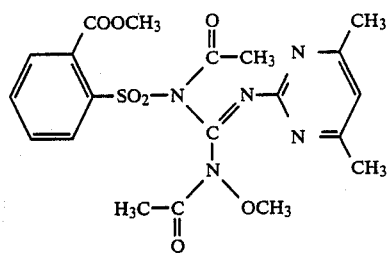

(Process (f/β))

A solution of 3.7 g (0.033 mol) of 1,4-diazabicyclo-[2,2,2]-octane in 30 ml of methylene chloride is added to a mixture of 3.9 g (0.01 mol) of N'-(4,6-dimethyl-pyrimidin-2-yl)-N''-methoxy-N'''-(2-methoxycarbonyl-benzenesulphonyl)-guanidine, 2.3 g (0.03 mol) of acetyl chloride and 30 ml of methylene chloride, while stirring, an internal temperature of between −20° C. and 0° C. being maintained. The reaction mixture is then stirred at about 20° C. for about 15 hours, without cooling, and is then washed with water, dried with sodium sulphate and filtered. The filtrate is concentrated and the residue is made to crystallize by trituration with diethyl ether.

1.8 g (38% of theory) of N'-(4,6-dimethyl-pyrimidin-2-yl)-N'',N''''-diacetyl-N''-methoxy-N'''-(2-methoxycarbonyl-benzenesulphonyl)-guanidine of melting point 134° C. are obtained.

The compounds of the formula (I) listed in the following Table 3 can be prepared analogously to Example 1 to 4 or process variant (a) to (f):

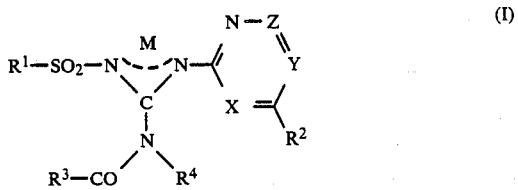

The compounds of the formula (I) in which M represents an acyl radical —COR⁷ can be allocated the general structure (ID)-see above-on the basis of their spectral data, as also happened in Example 4; however, it has not yet been possible completely to exclude the isomeric structure (IC).

TABLE 3

| Example No. | R¹ | R³ | R⁴ | R² | M | Melting point [°C.] |
|---|---|---|---|---|---|---|
| 5 | 2-Cl-phenyl | CH₃ | —OCH₂-phenyl | 4,6-dimethyl-pyrimidin-2-yl | H | 90 |
| 6 | 2-COOCH₃-phenyl | 4-O₂N-phenyl | —OCH₂-phenyl | 4,6-dimethyl-pyrimidin-2-yl | H | 148–149 |
| 7 | 2-COOCH₃-phenyl | 4-F-phenyl | —OCH₂-phenyl | 4,6-dimethyl-pyrimidin-2-yl | H | 142–145 |
| 8 | 2-COOCH₃-phenyl | 4-O₂N-phenyl | —OCH₃ | 4,6-dimethyl-pyrimidin-2-yl | —CO-(4-NO₂-phenyl) | 201–202 |
| 9 | 2-COOCH₃-phenyl | 4-O₂N-phenyl | —OCH₃ | 4,6-dimethoxy-pyrimidin-2-yl | —CO-(4-NO₂-phenyl) | 113 (decomposition) |

TABLE 3-continued

| Example No. | R¹ | R³ | R⁴ | (N=Z, X, Y, R²) | M | Melting point [°C.] |
|---|---|---|---|---|---|---|
| 10 | 2-COOCH₃-phenyl | 4-Cl-phenyl | —OCH₂-phenyl | 4-CH₃-pyrimidin-2-yl | H | 145 |
| 11 | 2-Cl-phenyl | 4-Cl-phenyl | —OCH₃ | 4,6-di-CH₃-pyrimidin-2-yl | H | 148 |
| 12 | 2-Cl-phenyl | 4-O₂N-phenyl | —OCH₃ | 4,6-di-CH₃-pyrimidin-2-yl | H | 156 |
| 13 | 2-COOCH₃-phenyl | 4-O₂N-phenyl | —OCH₃ | 4,6-di-CH₃-pyrimidin-2-yl | H | 163 |
| 14 | 2-Cl-phenyl | 2-Cl-phenyl | —OCH₃ | 4,6-di-CH₃-pyrimidin-2-yl | H | 158 |
| 15 | 2-COOCH₃-phenyl | 2-Cl-phenyl | —OCH₃ | 4,6-di-CH₃-pyrimidin-2-yl | H | 149 |
| 16 | 2-COOCH₃-phenyl | 2,4-di-Cl-phenyl | —OCH₃ | 4,6-di-CH₃-pyrimidin-2-yl | H | 149 |
| 17 | 2-COOCH₃-phenyl | 4-Br-phenyl | —OCH₃ | 4,6-di-CH₃-pyrimidin-2-yl | H | 143 |

TABLE 3-continued

| Example No. | R¹ | R³ | R⁴ | R² (N=Z, X, Y group) | M | Melting point [°C.] |
|---|---|---|---|---|---|---|
| 18 | 2-COOCH₃-phenyl | 2-Br-phenyl | —OCH₃ | 4,6-dimethylpyrimidin-2-yl | H | 155 |
| 19 | 2-COOCH₃-phenyl | 4-F-phenyl | —OCH₃ | 4,6-dimethylpyrimidin-2-yl | H | 155 |
| 20 | 2-COOCH₃-phenyl | 3-F-phenyl | —OCH₃ | 4,6-dimethylpyrimidin-2-yl | H | 148 |
| 21 | 2-Cl-phenyl | 2-F-phenyl | —OCH₃ | 4,6-dimethylpyrimidin-2-yl | H | 152 |
| 22 | 2-COOCH₃-phenyl | 2-F-phenyl | —OCH₃ | 4,6-dimethylpyrimidin-2-yl | H | 158 |
| 23 | 2-Cl-phenyl | 3-Br-phenyl | —OCH₃ | 4,6-dimethylpyrimidin-2-yl | H | 143 |
| 24 | 2-Cl-phenyl | 4-F-phenyl | —OCH₃ | 4,6-dimethylpyrimidin-2-yl | H | 147 |
| 25 | 2-Cl-phenyl | 4-F-phenyl | —OH | 4,6-dimethylpyrimidin-2-yl | H | 186 |

TABLE 3-continued

| Example No. | R¹ | R³ | R⁴ | (N=Z, Y, X, R²) | M | Melting point [°C.] |
|---|---|---|---|---|---|---|
| 26 | 2-Cl-C₆H₄ | 4-Cl-C₆H₄ | —OH | 2-CH₃, 4-CH₃, 6-CH₃ pyrimidinyl | H | 153 |
| 27 | 2-Cl-C₆H₄ | CH₃—CHCl— | —OCH₃ | 2-CH₃, 4-CH₃, 6-CH₃ pyrimidinyl | H | (oil) |
| 28 | 2-Cl-C₆H₄ | CCl₃— | —OCH₃ | 2-CH₃, 4-CH₃, 6-CH₃ pyrimidinyl | H | 128 |
| 29 | 2-COOCH₃-C₆H₄ | CCl₃— | —OCH₃ | 2-CH₃, 4-CH₃, 6-CH₃ pyrimidinyl | H | 148 |
| 30 | 2-COOCH₃-C₆H₄ | 4-O₂N-C₆H₄ | —OCH₃ | 2-CH₃, 4-CH₃, 6-OCH₃ pyrimidinyl | —CO-C₆H₄-4-NO₂ | |
| 31 | 2-COOCH₃-C₆H₄ | 2,4-Cl₂-C₆H₃ | —OCH₃ | 2-CH₃, 4-CH₃, 6-CH₃ pyrimidinyl | —CO-C₆H₃-2,4-Cl₂ | 155 |
| 32 | 2-COOCH₃-C₆H₄ | 4-F-C₆H₄ | —OCH₃ | 2-CH₃, 4-CH₃, 6-CH₃ pyrimidinyl | —CO-C₆H₄-4-F | 146 |
| 33 | 2-COOCH₃-C₆H₄ | 3-F-C₆H₄ | —OCH₃ | 2-CH₃, 4-CH₃, 6-CH₃ pyrimidinyl | —CO-C₆H₄-3-F | 151 |

TABLE 3-continued

| Example No. | R¹ | R³ | R⁴ | (ring structure with N–Z, X, Y, R²) | M | Melting point [°C.] |
|---|---|---|---|---|---|---|
| 34 | 2-COOCH₃-phenyl | phenyl-O– | –OCH₃ | 4,6-dimethylpyrimidin-2-yl (CH₃, CH₃) | H | 148 |
| 35 | 2-COOCH₃-phenyl | CH₃–NH– | –OCH₃ | 4,6-dimethylpyrimidin-2-yl (CH₃, CH₃) | H | 146 |
| 36 | 2-COOCH₃-phenyl | 4-Cl-phenyl-NH– | –OCH₃ | 4,6-dimethylpyrimidin-2-yl (CH₃, CH₃) | H | 173 |
| 37 | 2-OCF₃-phenyl | 2,4-dichlorophenyl | –OCH₃ | 4,6-dimethoxypyrimidin-2-yl (OCH₃, OCH₃) | H | 133 |
| 38 | 2-OCF₃-phenyl | CH₃NH– | –OCH₃ | 4,6-dimethoxypyrimidin-2-yl (OCH₃, OCH₃) | H |  |
| 39 | 2-COOCH₃-benzyl (–CH₂–) | CH₃ | –OCH₃ | 4,6-dimethoxypyrimidin-2-yl (OCH₃, OCH₃) | H |  |
| 40 | 2-COOCH₃-phenyl | phenyl | –N(CH₃)₂ | 4,6-dimethylpyrimidin-2-yl (CH₃, CH₃) | H | 199 |

Preparation of starting substances of the formula (V)

Example (V-1)

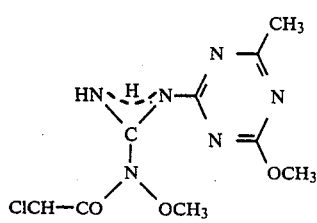

7.5 g (0.05 mol) of dichloroacetyl chloride are added to a mixture, kept at 0° C. to +5° C., of 8.8 g (0.05 mol) of N'-(4-methoxy-6-methyl-s-triazin-2-yl)-N''-methoxy-guanidine, 6.0 g (0.054 mol) of 1,4-diazabicyclo[2,2,2]-octane and 100 ml of methylene chloride. After the mixture has been stirred at 20° C. for 15 hours, it is washed with water, dried with sodium sulphate, filtered and concentrated under reduced pressure.

11.0 g (71% of theory) of N'-(4-methoxy-6-methyl-s-triazin-2-yl)-N''-methoxy-N''-dichloroacetyl-guanidine are obtained as a highly viscous oil (with a refractive index which cannot be determined).

Example (V-2)

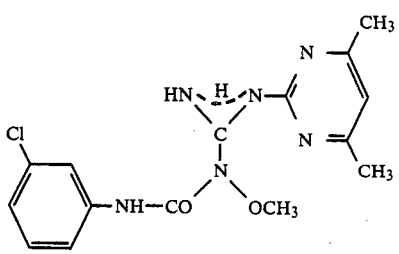

A mixture of 9.8 g (0.05 mol) of N'-(4,6-dimethyl-pyrimidin-2-yl)-N''-methoxy-guanidine, 7.7 g (0.05 mol) of 3-chloro-phenyl isocyanate and 80 ml of dioxane is stirred at 20° C. for one hour. The product obtained as crystals is isolated by filtration with suction.

12.0 g (69% of theory) of N'-(4,6-dimethyl-pyrimidin-2-yl)-N''-methoxy-N''-(3-chloro-phenylaminocarbonyl)guanidine of melting point 169° C. are obtained.

The following guanidine derivatives of the formula (V) can be prepared analogously to Example (V-1) and (V-2):

TABLE 4

$$\underset{R^3-CO}{\overset{HN}{\underset{N}{\diagdown}}}\overset{H}{\underset{C}{\diagdown}}\overset{N}{\underset{R^4}{\diagup}}\overset{N-Z}{\underset{X}{\diagup}}\overset{Y}{\underset{R^2}{\diagdown}}$$ (V)

| Example No. | R³ | R⁴ | $\overset{N-Z}{\underset{X}{\diagup}}\overset{Y}{\underset{R^2}{\diagdown}}$ R² | Melting point [°C.] |
|---|---|---|---|---|
| (V-3) | CH₃ | —OCH₃ | 4,6-dimethyl-pyrimidin-2-yl | 74–76 |
| (V-4) | phenyl | —OCH₃ | 4,6-dimethyl-pyrimidin-2-yl | 112–118 |
| (V-5) | CH₃—NH— | —OCH₃ | 4,6-dimethyl-pyrimidin-2-yl | 114 (decomposition) |

TABLE 4-continued $$\text{(V)}$$

Structure (V): HN-H-N-C(=N-Z)(Y)...X=R²; with C bearing NR³CO, R⁴, and HN-H-N groups.

| Example No. | R³ | R₄ | ![N-Z/Y/X=R²] R² | Melting point [°C.] |
|---|---|---|---|---|
| (V-6) | H₃C—⟨C₆H₄⟩—SO₂—NH— | —OCH₃ | pyrimidinyl with CH₃, CH₃ | 162 |
| (V-7) | O₂N—⟨C₆H₄⟩— | —OCH₃ | pyrimidinyl with CH₃, CH₃ | 148 |
| (V-8) | Cl—⟨C₆H₄⟩—NH— | —OCH₃ | pyrimidinyl with CH₃, OCH₃ | |

Example A

Pre-emergence test/greenhouse

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (Like untreated control)
100% = total destruction

In this test, for example, the following compounds from the preparation examples exhibit a very good activity: (16), (17), (18), (20) and (22).

Example B

Post-emergence test/greenhouse

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, the following compounds from the preparation examples exhibit very good activity against weeds: (12), (13) and (18).

Compound (12) also exhibits an excellent tolerance in wheat.

We claim:
1. An acylated sulphonylguanidine of the formula

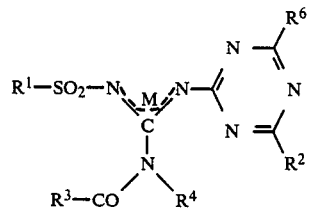

in which
R¹ represents an optionally substituted radical from the group consisting of alkyl, aralkyl and aryl with in each case up to 10 carbon atoms,
R² represents hydrogen, halogen, hydroxyl, $C_1$-$C_4$-alkyl, $C_1$-$C_4$-halogenoalkyl, $C_1$-$C_4$-alkoxy, $C_1$-$C_4$-halogenoalkoxy, $C_1$-$C_4$-alkylthio, $C_1$-$C_4$-halogenoalkylthio, amino, $C_1$-$C_4$-alkylamino or di-($C_1$-$C_4$-alkyl)-amino,
R⁵ represents hydrogen, halogen, cyano, $C_1$-$C_4$-alkyl, formyl, $C_1$-$C_4$-alkyl-carbonyl or $C_1$-$C_4$-alkoxy-carbonyl,
R⁶ represents hydrogen, halogen, hydroxyl, $C_1$-$C_4$-alkyl, $C_1$-$C_4$-alkoxy, $C_1$-$C_4$-alkylthio, $C_1$-$C_4$-alkylamino or di-($C_1$-$C_4$-alkyl)-amino,
R³ represents a radical R⁷, or represents a radical —NHR⁸,
R⁷ represents an optionally substituted radical from the group consisting of alkyl, alkenyl, alkinyl, alkoxy, alkenyloxy, alkinyloxy, cycloalkyl, dialkylamino, aralkyl, aryl, aralkoxy, aryloxy, alkylthio, aralkylthio and arylthio with in each case up to 10 carbon atoms,
R⁸ represents an optionally substituted radical from the group consisting of alkyl, cycloalkyl, aralkyl, aryl and arylsulphonyl with in each case up to 10 carbon atoms,
R⁴ represents hydrogen, or represents an optionally substituted radical from the group consisting of alkyl, alkenyl, alkinyl, cycloalkyl, aralkyl and aryl with in each case up to 10 carbon atoms, or
R⁴ represents the radical —OR⁹ or —NR¹⁰R¹¹,
R⁹ represents hydrogen or an optionally substituted radical from the group consisting of alkyl, alkenyl, alkinyl, cycloalkyl, cycloalkylalkyl, aralkyl and aryl with in each case up to 10 carbon atoms,
R¹⁰ represents hydrogen or $C_1$-$C_4$-alkyl,
R¹¹ represents hydrogen or an optionally substituted radical from the group consisting of alkyl, alkenyl, alkinyl, cycloalkyl, aralkyl, aryl, alkylcarbonyl, alkoxycarbonyl, alkylsulphonyl and arylsulphonyl with in each case up to 10 carbon atoms, and
M represents hydrogen or one equivalent of a metal or represents the radical —COR⁷, the optional substituents when present being selected from the group consisting of fluorine, chlorine, bromine, cyano, nitro, $C_1$-$C_4$-alkoxycarbonyl, di-($C_1$-$C_4$-alkyl)-amino-carbonyl, $C_1$-$C_4$-alkoxy, $C_1$-$C_4$-alkylthio, $C_1$-$C_4$-alkylsulphinyl and $C_1$-$C_4$-alkylsulphonyl,
or a strong acid adduct thereof.

2. A compound according to claim 1, in which R¹ represents the radical

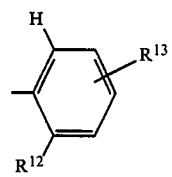

wherein
R¹² and R¹³ are identical or different and represent hydrogen, halogen, cyano, nitro or $C_1$-$C_6$-alkyl (which is optionally substituted by fluorine, chlorine, bromine, cyano, carboxyl, $C_1$-$C_4$-alkoxycarbonyl, $C_1$-$C_4$-alkylamino-carbonyl, di-($C_1$-$C_4$-alkyl)-amino-carbonyl, hydroxyl, $C_1$-$C_4$-alkoxy, formyloxy, $C_1$-$C_4$-alkylcarbonyloxy, $C_1$-$C_4$-alkoxy-carbonyloxy, $C_1$-$C_4$-alkylamino-carbonyloxy, $C_1$-$C_4$-alkylthio, $C_1$-$C_4$-alkylsulphinyl, $C_1$-$C_4$-alkylsulphonyl, di-($C_1$-$C_4$-alkyl)-aminosulphonyl, $C_3$-$C_6$-cycloalkyl or phenyl), or represent $C_2$-$C_6$-alkenyl (which is optionally substituted by fluorine, chlorine, bromine, cyano, $C_1$-$C_4$-alkoxycarbonyl, carboxyl or phenyl), or represent $C_2$-$C_6$-alkinyl (which is optionally substituted by fluorine, chlorine, bromine, cyano, $C_1$-$C_4$-alkoxy-carbonyl, carboxyl or phenyl), or represent $C_1$-$C_4$-alkoxy (which is optionally substituted by fluorine, chlorine, bromine, cyano, carboxyl, $C_1$-$C_4$-alkoxy-carbonyl, $C_1$-$C_4$-alkoxy, $C_1$-$C_4$-alkylthio, $C_1$-$C_4$-alkylsulphinyl or $C_1$-$C_4$-alkylsulphonyl), or represent $C_1$-$C_4$-alkylthio (which is optionally substituted by fluorine, chlorine, bromine, cyano, carboxyl, $C_1$-$C_4$-alkoxycarbonyl, $C_1$-$C_4$-alkylthio, $C_1$-$C_4$-alkylsulphinyl or $C_1$-$C_4$-alkylsulphonyl), or represent $C_3$-$C_6$-alkenyloxy (which is optionally substituted by fluorine, chlorine, bromine, cyano or $C_1$-$C_4$-alkoxy-carbonyl), or represent $C_2$-$C_6$-alkenylthio (which is optionally substituted by fluorine, chlorine, bromine, cyano, nitro, $C_1$-$C_3$-alkylthio or $C_1$-$C_4$-alkoxycarbonyl), $C_3$-$C_6$-alkinyloxy or $C_3$-$C_6$-alkinylthio, or represent the radical —S(O)$_p$—R¹⁴,
wherein
p represents the number 1 or 2 and
R¹⁴ represents $C_1$-$C_4$-alkyl (which is optionally substituted by fluorine, chlorine, bromine, cyano or $C_1$-$C_4$-alkoxy-carbonyl), $C_3$-$C_6$-alkenyl, $C_3$-$C_6$-alkinyl, $C_1$-$C_4$-alkoxy, $C_1$-$C_4$-alkoxyamino, $C_1$-$C_4$-alkoxy-$C_1$-$C_4$-alkylamino, $C_1$-$C_4$-alkylamino or di-($C_1$-$C_4$-alkyl)-amino, or
R¹² and R¹³ furthermore represent phenyl or phenoxy, or represent $C_1$-$C_4$-alkylcarbonylamino, $C_1$-$C_4$-alkoxy-carbonylamino, $C_1$-$C_4$-alkylaminocarbonyl-amino or di-($C_1$-$C_4$-alkyl)-aminocarbonylamino, or represent the radical —CO—R¹⁵,
wherein
R¹⁵ represents $C_1$-$C_6$-alkyl, $C_1$-$C_6$-alkoxy, $C_3$-$C_6$-cycloalkoxy, $C_3$-$C_6$-alkenyloxy, $C_1$-$C_4$-alkylthio, $C_1$-$C_4$-alkylamino, $C_1$-$C_4$-alkoxyamino, $C_1$-$C_4$-alkoxy-$C_1$-$C_4$-alkyl-amino or di-($C_1$-$C_4$-alkyl)-amino (which are optionally substituted by fluorine and/or chlorine), or $R^{12}$ and $R^{13}$ furthermore represent $C_1-C_4$-alkylsulphonyloxy or di-($C_1-C_4$-alkyl)-aminosulphonylamino, or represent the radical —CH=N—$R^{16}$, wherein $R^{16}$ represents $C_1-C_6$-alkyl which is optionally substituted by fluorine, chlorine, cyano, carboxyl, $C_1-C_4$-alkoxy, carbonyl, $C_1-C_4$-alkylthio, $C_1-C_4$-alkylsulphinyl or $C_1-C_4$-alkylsulphonyl, or represents benzyl which is optionally substituted by fluorine or chlorine, or represents $C_3-C_6$-alkenyl or $C_3-C_6$-alkinyl, each of which is optionally substituted by fluorine or chlorine, or represents phenyl which is optionally substituted by fluorine, chlorine, bromine, $C_1-C_4$-alkyl, $C_1-C_4$-alkoxy, trifluoromethyl, trifluoromethoxy or trifluoromethylthio, or represents $C_1-C_6$-alkoxy, $C_3-C_6$-alkenoxy, $C_3-C_6$-alkinoxy or benzyloxy, each of which is optionally substituted by fluorine and/or chlorine, or represents amino, $C_1-C_4$-alkylamino, di-($C_1-C_4$-alkyl)-amino, phenylamino, $C_1-C_4$-alkylcarbonyl-amino, $C_1-C_4$-alkoxy-carbonylamino or $C_1-C_4$-alkylsulphonylamino, or represents phenylsulphonylamino which is optionally substituted by fluorine, chlorine, bromine or methyl, $R^1$ represents the radical

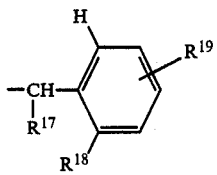

wherein $R^{17}$ represents hydrogen or $C_1-C_4$-alkyl and $R^{18}$ and $R^{19}$ are identical or different and represent hydrogen, fluorine, chlorine, bromine, nitro, cyano, $C_1-C_4$-alkyl (which is optionally substituted by fluorine and/or chlorine), $C_1-C_4$-alkoxy (which is optionally substituted by fluorine and/or chlorine), carboxyl, $C_1-C_4$-alkoxycarbonyl, $C_1-C_4$-alkylsulphonyl or di-($C_1-C_4$-alkyl)-aminosulphonyl;

or $R^1$ represents the radical

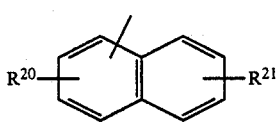

wherein $R^{20}$ and $R^{21}$ are identical or different and represent hydrogen, fluorine, chlorine, bromine, nitro, cyano, $C_1-C_4$-alkyl (which is optionally, substituted by fluorine and/or chlorine) or $C_1-C_4$-alkoxy (which is optionally substituted by fluorine and/or chlorine);

$R^2$ represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino, $R^5$ represents hydrogen, fluorine, chlorine, bromine, cyano, methyl, formyl, acetyl, methoxycarbonyl or ethoxycarbonyl, and $R^6$ represents hydrogen, fluorine, chlorine, bromine, methyl, ethyl, methoxy, ethoxy, propoxy, isopropoxy, methylthio, ethylthio, methylamino, ethylamino, dimethylamino or diethylamino, $R^3$ represents the radical $R^7$, or represents a radical —$NHR^8$, wherein $R^7$ represents $C_1-C_8$-alkyl, $C_1-C_8$-alkoxy or $C_1-C_8$-alkylthio (which are optionally substituted by fluorine, chlorine, bromine, cyano, nitro, $C_1-C_4$-alkoxy-carbonyl, di-($C_1-C_4$-alkyl)-aminocarbonyl, $C_1-C_4$-alkoxy, $C_1-C_4$-alkylthio, $C_1-C_4$-alkylsulphinyl 0r $C_1-C_4$-alkylsulphonyl), or represents $C_2-C_8$-alkenyl or $C_2-C_8$-alkinyl (which are optionally substituted by fluorine, chlorine, bromine, cyano, nitro, $C_1-C_4$-alkoxy, $C_1-C_4$-alkylthio or phenyl), or represents $C_2-C_8$-alkenyloxy or $C_2-C_8$-alkinyloxy (which are optionally substituted by fluorine, chlorine, bromine, cyano, nitro, $C_1-C_4$-alkoxy, $C_1-C_4$-alkylthio or phenyl), or represents $C_3-C_6$-cycloalkyl or di-($C_1-C_4$-alkyl)-amino (which is optionally substituted by fluorine, chlorine, bromine, cyano, nitro, phenyl, phenoxy, $C_1-C_4$-alkoxy, $C_1-C_4$-alkylthio, $C_1-C_4$-alkylsulphinyl or $C_1-C_4$-alkylsulphonyl), or represents phenoxy or benzyloxy, or represents phenylthio or benzylthio (which are optionally substituted by fluorine, chlorine, bromine, $C_1-C_4$-alkyl, trifluoromethyl, $C_1-C_4$-alkoxy, $C_1-C_2$-fluoroalkoxy, $C_1-C_4$-alkylthio, $C_1-C_4$-alkylsulphinyl, $C_1-C_4$-alkylsulphonyl, cyano, nitro and/or $C_1-C_4$-alkoxycarbonyl), or represents benzyl or phenyl (which are optionally substituted by one or more radicals from the group consisting of halogen, cyano, nitro, $C_1-C_4$-alkyl (which is optionally substituted by fluorine, chlorine, bromine, cyano, carboxyl, $C_1-C_4$-alkoxy-carbonyl, di-($C_1-C_4$-alkyl)-aminocarbonyl, $C_1-C_4$-alkoxy, formyloxy, $C_1-C_4$-alkyl-carbonyloxy, $C_1-C_4$-alkoxy-carbonyloxy, $C_1-C_4$-alkylthio, $C_1-C_4$-alkylsulphinyl, $C_1-C_4$-alkylsulphonyl, di-($C_1-C_4$-alkyl)-aminosulphonyl or phenyl), $C_2-C_6$-alkenyl (which is optionally substituted by fluorine, chlorine, bromine, cyano, $C_1-C_4$-alkoxycarbonyl, carboxyl or phenyl), $C_2-C_6$-alkinyl (which is optionally substituted by fluorine, chlorine, bromine, cyano, $C_1-C_4$-alkoxy-carbonyl or phenyl), $C_1-C_4$-alkoxy (which is optionally substituted by fluorine, chlorine, bromine, cyano, carboxyl, $C_1-C_4$-alkoxy-carbonyl, $C_1-C_4$-alkylthio, $C_1-C_4$-alkylsulphinyl or $C_1-C_4$-alkylsulphonyl), $C_3-C_6$-alkenoxy (which is optionally substituted by fluorine, chlorine, bromine, cyano or $C_1-C_4$-alkoxy-carbonyl), $C_3-C_6$-alkenylthio (which is optionally substituted by fluorine, chlorine, bromine, cyano or $C_1-C_4$-alkoxy-carbonyl), $C_1-C_4$-alkylthio, $C_1-C_4$-alkylsulphinyl or $C_1-C_4$-alkylsulphonyl (which are optionally substituted by fluorine, chlorine, bromine, cyano or $C_1-C_4$-alkoxy-carbonyl), phenyl, phenoxy, di-($C_1-C_4$-alkyl)-amino-sulphonyl, $C_1-C_6$-alkoxy-carbonyl, $C_3-C_6$-cycloalkoxy-carbonyl or di-($C_1-C_4$-alkyl)amino-carbonyl, and/or are optionally benzofused), and $R^8$ represents $C_1-C_6$-alkyl, cyclohexyl, benzyl, phenyl, naphthyl, phenylsulphonyl or naphthylsulphonyl (the aromatic radicals mentioned optionally being substituted by fluorine, chlorine, bromine, $C_1$-$C_4$-alkyl, $C_1$-$C_4$-alkoxy, trifluoromethyl, $C_1$-$C_2$-fluoroalkoxy, $C_1$-$C_2$-chlorofluoroalkoxy, $C_1$-$C_2$-chloroalkoxy, $C_1$-$C_4$-alkylthio, $C_1$-$C_4$-alkylsulphinyl, $C_1$-$C_4$-alkylsulphonyl, dimethylaminosulphonyl, N-methoxy-N-methylaminosulphonyl and/or $C_1$-$C_4$-alkoxycarbonyl);

$R^4$ represents hydrogen, $C_1$-$C_6$-alkyl (which is optionally substituted by fluorine, chlorine, bromine, cyano, carboxyl, $C_1$-$C_4$-alkoxy-carbonyl, hydroxyl or $C_1$-$C_4$-alkoxy), $C_3$-$C_6$-cycloalkyl, $C_3$-$C_6$-alkenyl, $C_3$-$C_6$-alkinyl, phenylethyl or benzyl (which is optionally substituted by fluorine, chlorine, nitro, cyano, $C_1$-$C_4$-alkyl, $C_1$-$C_4$-alkoxy or $C_1$-$C_4$-alkoxy-carbonyl), or represents phenyl (which is optionally substituted by fluorine, chlorine, bromine, hydroxyl, cyano, nitro, amino, $C_1$-$C_4$-alkyl, trifluoromethyl, $C_1$-$C_4$-alkoxy, trifluoromethoxy, $C_1$-$C_4$-alkylthio, trifluoromethylthio, aminosulphonyl or $C_1$-$C_4$-alkoxy-carbonyl), or $R^4$ represents the radical $-OR^9$, wherein $R^9$ represents hydrogen, $C_1$-$C_8$-alkyl (which is optionally substituted by fluorine, chlorine, $C_1$-$C_4$-alkoxy, $C_1$-$C_4$-alkylthio, $C_1$-$C_4$-alkylsulphinyl, $C_1$-$C_4$-alkylsulphonyl, carboxyl, cyano or nitro), $C_3$-$C_6$-alkenyl (which is optionally substituted by fluorine or chlorine), $C_3$-$C_6$-alkinyl, $C_3$-$C_6$-cycloalkyl, $C_3$-$C_6$-cycloalkyl-$C_1$-$C_2$-alkyl, $C_1$-$C_4$-alkoxy-carbonyl-$C_1$-$C_2$-alkyl, aminocarbonyl-$C_1$-$C_2$-alkyl, $C_1$-$C_4$-alkylaminocarbonyl-$C_1$-$C_2$-alkyl, di-($C_1$-$C_4$-alkyl)aminocarbonyl-$C_1$-$C_2$-alkyl, or represents phenyl, phenylethyl, benzhydryl or benzyl (which are optionally substituted by fluorine, chlorine, bromine, cyano, nitro, $C_1$-$C_4$-alkyl, $C_1$-$C_4$-alkoxy, carboxyl or $C_1$-$C_4$-alkoxycarbonyl), $R^4$ represents the radical

wherein $R^{10}$ represents hydrogen or $C_1$-$C_4$-alkyl and $R^{11}$ represents hydrogen, $C_1$-$C_4$-alkyl (which is optionally substituted by halogen, cyano, nitro, $C_1$-$C_4$-alkoxy or $C_1$-$C_4$-alkoxy-carbonyl), $C_3$-$C_6$-cycloalkyl, phenyl-$C_1$-$C_2$-alkyl or phenyl (which are optionally substituted by halogen, cyano, nitro, $C_1$-$C_4$-alkyl, $C_1$-$C_2$-halogenoalkyl, $C_1$-$C_4$-alkoxy, $C_1$-$C_2$-halogenoalkoxy, $C_1$-$C_4$-alkylthio, $C_1$-$C_2$-halogenoalkylthio or $C_1$-$C_4$-alkoxy-carbonyl), or represents $C_1$-$C_4$-alkyl-carbonyl, $C_1$-$C_4$-alkoxycarbonyl, $C_1$-$C_4$-alkylsulphonyl, $C_1$-$C_4$-halogenoalkylsulphonyl or phenylsulphonyl (which is optionally substituted by halogen, cyano, nitro, $C_1$-$C_4$-alkyl, $C_1$-$C_4$-halogenoalkyl, $C_1$-$C_4$-alkoxy, $C_1$-$C_2$-halogenoalkoxy or $C_1$-$C_4$-alkoxy-carbonyl), and M represents hydrogen or one equivalent of sodium, potassium or calcium, or represents the radical $-COR^7$, or an adduct thereof with a hydrogen halide acid, sulphuric acid, an alkanesulphonic acid having 1 to 4 carbon atoms and optionally substituted by fluorine and/or chlorine, or a benzene- or naphthalenesulphonic acid which is optionally substituted by fluorine, chlorine, bromine or methyl.

3. A compound or adduct according to claim 1, in which $R^1$ represents the radical

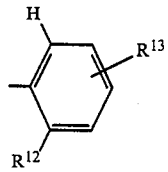

wherein $R^{12}$ represents fluorine, chlorine, bromine, methyl, trifluoromethyl, methoxy, difluoromethoxy, trifluoromethoxy, $C_1$-$C_3$-alkylthio, difluoromethylthio, trifluoromethylthio, $C_1$-$C_3$-alkylsulphinyl, $C_1$-$C_3$-alkylsulphonyl, dimethylaminosulphonyl, diethylaminosulphonyl, N-methoxy-N-methylaminosulphonyl, phenyl, phenoxy, $C_1$-$C_3$-alkoxy-carbonyl, $C_1$-$C_3$-alkoxyamino-sulphonyl, $C_1$-$C_3$-alkoxyamino-carbonyl or $C_1$-$C_3$-alkylamino-carbonyl, $R^{13}$ represents hydrogen, $R^2$ represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino, $R^5$ represents hydrogen, fluorine, chlorine, bromine, methyl, formyl, acetyl, methoxycarbonyl or ethoxycarbonyl, $R^6$ represents hydrogen, fluorine, chlorine, bromine, methyl, ethyl, methoxy, ethoxy, propoxy, isopropoxy, methylthio, ethylthio, methylamino, ethylamino, dimethylamino or diethylamino, $R^3$ represents $R^7$ or $-NHR^8$, $R^7$ represents $C_1$-$C_4$-alkyl (which is optionally substituted by fluorine and/or chlorine), or represents di-($C_1$-$C_2$-alkyl)-amino, or represents benzyl or phenyl (which are optionally substituted by fluorine, chlorine, bromine, cyano, nitro, $C_1$-$C_4$-alkyl, trifluoromethyl, $C_1$-$C_4$-alkoxy, trifluoromethoxy, difluoromethoxy, $C_1$-$C_4$-alkylthio, $C_1$-$C_4$-alkoxycarbonyl, $C_1$-$C_4$-alkylsulphinyl, $C_1$-$C_4$-alkylsulphonyl, dimethylaminosulphonyl, phenyl or phenoxy), $R^8$ represents $C_1$-$C_4$-alkyl, cyclohexyl, benzyl, phenyl or phenylsulphonyl (the phenyl radicals optionally being substituted by fluorine, chlorine, $C_1$-$C_2$-alkyl, $C_1$-$C_2$-alkoxy, trifluoromethyl, trifluoromethoxy, chlorofluoromethoxy, chlorodifluoromethoxy, dichloromethoxy, 2-chloroethoxy, $C_1$-$C_2$-alkylthio, $C_1$-$C_2$-alkylsulphinyl, $C_1$-$C_2$-alkylsulphonyl, dimethylaminosulphonyl, N-methoxy-N-methylaminosulphonyl and/or $C_1$-$C_2$-alkoxycarbonyl), $R^4$ represents the radical $-O-R^9$, $R^9$ represents $C_1$-$C_4$-alkyl (which is optionally substituted by fluorine or chlorine), or represents $C_3$-$C_6$-alkenyl (which is optionally substituted by chlorine), or represents $C_1$-$C_3$-alkoxy-carbonyl-$C_1$-$C_2$- alkyl, phenyl, phenylethyl or benzyl (which are optionally substituted by fluorine, chlorine, nitro, methyl, methoxy or $C_1$-$C_2$-alkoxy-carbonyl);

or $R^4$ represents the radical

wherein $R^{10}$ represents hydrogen or methyl and $R^{11}$ represents hydrogen or $C_1$-$C_3$-alkyl (which is optionally substituted by fluorine, chlorine, cyano, $C_1$-$C_2$-alkoxy or $C_1$-$C_2$-alkoxy-carbonyl), or represents $C_3$-$C_6$-cycloalkyl, phenyl, benzyl or phenylethyl (which are optionally substituted by fluorine, chlorine, bromine, nitro, cyano, $C_1$-$C_2$-alkyl, $C_1$-$C_2$-alkoxy or $C_1$-$C_2$-alkoxy-carbonyl), or represents acetyl, methoxycarbonyl, benzenesulphonyl or toluenesulphonyl;

M represents hydrogen or one equivalent of sodium, potassium or calcium, or represents the radical —$COR^7$.

4. A compound according to claim 1, wherein such compound is N'-(4-methoxy-6-methyl-s-triazin-2-yl)-N''-dimethylamino-N'''-(4-chloro-phenylamino-carbonyl)-N''''-(2-chloro-benzenesulphonyl)-guanidine of the formula

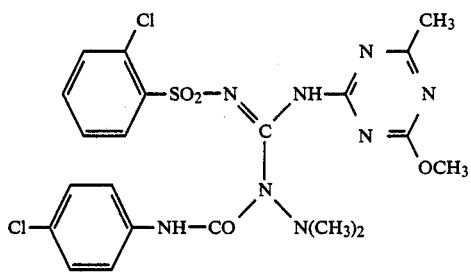

or a strong acid adduct thereof.

5. A compound according to claim 1, wherein such compound is N'-(4-methoxy-6-methyl-s-triazin-2-yl)-N''-methoxy-N''-dichloroacetyl-N'''-(2-methoxycarbonylbenzenesulphonyl)-guanidine of the formula

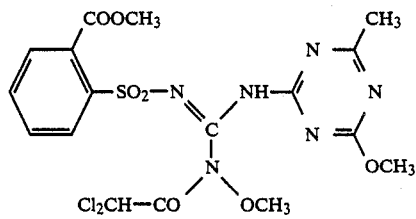

or a strong acid adduct thereof.

6. A compound according to claim 1 of the formula

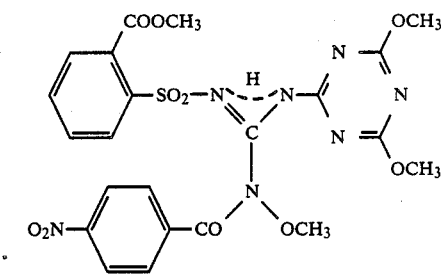

7. The method according to claim 9, wherein such compound is

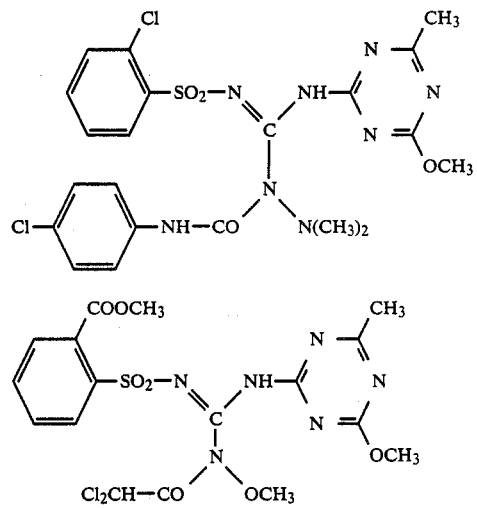

or

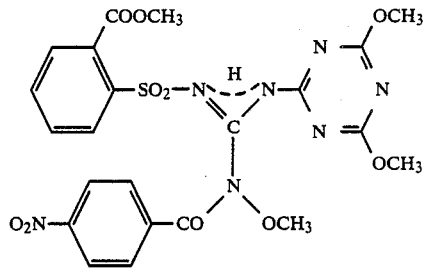

8. A herbicidal composition comprising a herbicidally effective amount of a compound or adduct according to claim 1 and a diluent.

9. A method of combating unwanted vegetation which comprises applying to such vegetation or to a locus from which it is desired to exclude such vegetation a herbicidally effective amount of a compound or adduct according to claim 1.

10. A guanidine derivative of the formula

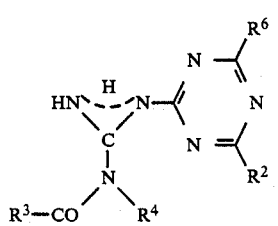

in which
- $R^2$ represents hydrogen, halogen, hydroxyl, $C_1$-$C_4$-alkyl, $C_1$-$C_4$-halogenoalkyl, $C_1$-$C_4$-alkoxy, $C_1$-$C_4$-halogenoalkoxy, $C_1$-$C_4$-alkylthio, $C_1$-$C_4$-halogenoalkylthio, amino, $C_1$-$C_4$-alkylamino or di-($C_1$-$C_4$-alkyl)-amino,
- $R^5$ represents hydrogen, halogen, cyano, $C_1$-$C_4$-alkyl, formyl, $C_1$-$C_4$-alkyl-carbonyl or $C_1$-$C_4$-alkoxy-carbonyl,
- $R^6$ represents hydrogen, halogen, hydroxyl, $C_1$-$C_4$-alkyl, $C_1$-$C_4$-alkoxy, $C_1$-$C_4$-alkylthio, $C_1$-$C_4$-alkylamino or di-($C_1$-$C_4$-alkyl)-amino,
- $R^3$ represents a radical $R^7$, or represents a radical —$NHR^8$,
- $R^7$ represents an optionally substituted radical from the group consisting of alkyl, alkenyl, alkinyl, alkoxy, alkenyloxy, alkinyloxy, cycloalkyl, dialkylamino, aralkyl, aryl, aralkoxy, aryloxy, alkylthio, aralkylthio and arylthio with in each case up to 10 carbon atoms,
- $R^8$ represents an optionally substituted radical from the group consisting of alkyl, cycloalkyl, aralkyl, aryl and arylsulphonyl with in each case up to 10 carbon atoms,
- $R^4$ represents hydrogen, or represents an optionally substituted radical from the group consisting of alkyl, alkenyl, alkinyl, cycloalkyl, aralkyl and aryl with in each case up to 10 carbon atoms, or
- $R^4$ represents the radical —$OR^9$ or —$NR^{10}R^{11}$,
- $R^9$ represents hydrogen or an optionally substituted radical from the group consisting of alkyl, alkenyl, alkinyl, cycloalkyl, cycloalkylalkyl, aralkyl and aryl with in each case up to 10 carbon atoms,
- $R^{10}$ represents hydrogen or $C_1$-$C_4$-alkyl, and
- $R^{11}$ represents hydrogen or an optionally substituted radical from the group consisting of alkyl, alkenyl, alkinyl, cycloalkyl, aralkyl, aryl, alkylcarbonyl, alkoxycarbonyl, alkylsulphonyl and arylsulphonyl with in each case up to 10 carbon atoms, the optional substituents when present being selected from the group consisting of fluorine, chlorine, bromine, cyano, nitro, $C_1$-$C_4$-alkoxycarbonyl, di-($C_1$-$C_4$-alkyl)-amino-carbonyl, $C_1$-$C_4$-alkoxy, $C_1$-$C_4$-alkylthio, $C_1$-$C_4$-alkylsulphinyl and $C_1$-$C_4$-alkylsulphonyl.

* * * * *